United States Patent
Prabhu

(10) Patent No.: US 10,426,616 B2
(45) Date of Patent: Oct. 1, 2019

(54) CARDIAC IMPLANT DELIVERY SYSTEM

(71) Applicant: Evalve, Inc., Santa Clara, CA (US)

(72) Inventor: Santosh V. Prabhu, Sunnyvale, CA (US)

(73) Assignee: Evalve, Inc., Santa Clara, CA (US)

(*) Notice: Subject to any disclaimer, the term of this patent is extended or adjusted under 35 U.S.C. 154(b) by 292 days.

(21) Appl. No.: 15/354,644

(22) Filed: Nov. 17, 2016

(65) Prior Publication Data

US 2018/0133007 A1    May 17, 2018

(51) Int. Cl.
| | | |
|---|---|---|
| *A61F 2/24* | (2006.01) | |
| *A61B 90/00* | (2016.01) | |
| *A61M 25/01* | (2006.01) | |
| *A61F 2/97* | (2013.01) | |
| *A61F 2/48* | (2006.01) | |

(Continued)

(52) U.S. Cl.
CPC ............ *A61F 2/2436* (2013.01); *A61B 90/06* (2016.02); *A61F 2/2439* (2013.01); *A61F 2/97* (2013.01); *A61M 25/0136* (2013.01); *A61M 25/0147* (2013.01); *A61M 25/0158* (2013.01); *A61B 2090/066* (2016.02); *A61F 2002/485* (2013.01); *A61F 2002/9517* (2013.01); *A61F 2002/9665* (2013.01); *A61F 2250/0071* (2013.01)

(58) Field of Classification Search
CPC ........ A61F 2/2436; A61F 2/2439; A61F 2/97; A61F 2002/9665; A61F 2002/9517; A61F 2002/485; A61F 2250/0071; A61B 90/06; A61B 2090/066; A61M 25/0136; A61M 25/0158; A61M 25/0147
See application file for complete search history.

(56) References Cited

U.S. PATENT DOCUMENTS

| | | |
|---|---|---|
| 1,996,261 A | 4/1935 | Storz |
| 2,097,018 A | 10/1937 | Chamberlain |
| 2,108,206 A | 2/1938 | Meeker |

(Continued)

FOREIGN PATENT DOCUMENTS

| | | |
|---|---|---|
| DE | 3504292 | 7/1986 |
| DE | 10116168 | 11/2001 |

(Continued)

OTHER PUBLICATIONS

Abe et al, De Vega's Annuloplasty for Acquired Tricuspid Disease: Early and Late Results in 110 Patients, Ann. Thorac. Surg., Jan. 1989, pp. 670-676, vol. 48.

(Continued)

*Primary Examiner* — Amy R Weisberg
(74) *Attorney, Agent, or Firm* — Workman Nyddeger

(57) ABSTRACT

The present disclosure relates to delivery systems for delivering and deploying interventional devices to a targeted area within a body, such as delivering a replacement heart valve to a targeted heart valve. A delivery device includes a steerable catheter and a replacement valve delivery system positioned within the steerable catheter and configured to be translatable within the steerable catheter. The steerable catheter includes one or more control wires running from a distal end of the catheter to a handle at the proximal end of the catheter. Each control wire is coupled to a control of the handle such that manipulation of the control provides deflection and control of the steerable catheter.

20 Claims, 18 Drawing Sheets

(51) Int. Cl.
*A61F 2/95* (2013.01)
*A61F 2/966* (2013.01)

(56) References Cited

U.S. PATENT DOCUMENTS

| | | | |
|---|---|---|---|
| 3,296,668 A | 1/1967 | Aiken | |
| 3,378,010 A | 4/1968 | Codling et al. | |
| 3,557,780 A | 1/1971 | Sato | |
| 3,671,979 A | 6/1972 | Moulopoulos | |
| 3,675,639 A | 7/1972 | Cimber | |
| 3,874,338 A | 4/1975 | Happel | |
| 4,007,743 A | 2/1977 | Blake | |
| 4,056,854 A | 11/1977 | Boretos et al. | |
| 4,064,881 A | 12/1977 | Meredith | |
| 4,091,815 A | 5/1978 | Larsen | |
| 4,112,951 A | 9/1978 | Hulka et al. | |
| 4,235,238 A | 11/1980 | Ogiu et al. | |
| 4,297,749 A | 11/1981 | Davis et al. | |
| 4,458,682 A | 7/1984 | Cerwin | |
| 4,425,908 A | 11/1984 | Simon | |
| 4,484,579 A | 11/1984 | Meno et al. | |
| 4,487,205 A | 12/1984 | Di Giovanni et al. | |
| 4,498,476 A | 2/1985 | Cerwin et al. | |
| 4,510,934 A | 4/1985 | Batra | |
| 4,531,522 A | 7/1985 | Bedi et al. | |
| 4,578,061 A | 3/1986 | Lemelson | |
| 4,641,366 A | 2/1987 | Yokoyama et al. | |
| 4,686,965 A | 8/1987 | Bonnet et al. | |
| 4,777,951 A | 10/1988 | Cribier et al. | |
| 4,809,695 A | 3/1989 | Gwathmey et al. | |
| 4,878,495 A | 11/1989 | Grayzel | |
| 4,917,089 A | 4/1990 | Sideris | |
| 4,944,295 A | 7/1990 | Gwathmey et al. | |
| 4,969,890 A | 11/1990 | Sugita et al. | |
| 4,994,077 A | 2/1991 | Dobben | |
| 5,015,249 A | 5/1991 | Nakao et al. | |
| 5,019,096 A | 5/1991 | Fox, Jr. et al. | |
| 5,042,707 A | 8/1991 | Taheri | |
| 5,047,041 A | 9/1991 | Samuels | |
| 5,049,153 A | 9/1991 | Nakao et al. | |
| 5,061,277 A | 10/1991 | Carpentier et al. | |
| 5,069,679 A | 12/1991 | Taheri | |
| 5,108,368 A | 4/1992 | Hammerslag et al. | |
| 5,125,758 A | 6/1992 | DeWan | |
| 5,171,252 A | 12/1992 | Friedland | |
| 5,171,259 A | 12/1992 | Inoue | |
| 5,190,554 A | 3/1993 | Coddington et al. | |
| 5,195,968 A | 3/1993 | Lundquist et al. | |
| 5,201,757 A * | 4/1993 | Heyn | A61F 2/95 606/198 |
| 5,209,756 A | 5/1993 | Seedhom et al. | |
| 5,226,429 A | 7/1993 | Kuzmak | |
| 5,226,911 A | 7/1993 | Chee et al. | |
| 5,234,437 A | 8/1993 | Sepetka | |
| 5,242,456 A | 9/1993 | Nash et al. | |
| 5,250,071 A | 10/1993 | Palermo | |
| 5,251,611 A | 10/1993 | Zehel et al. | |
| 5,254,130 A | 10/1993 | Poncet et al. | |
| 5,261,916 A | 11/1993 | Engelson | |
| 5,271,381 A | 12/1993 | Ailinger et al. | |
| 5,275,578 A | 1/1994 | Adams | |
| 5,282,845 A | 2/1994 | Bush et al. | |
| 5,304,131 A | 4/1994 | Paskar | |
| 5,306,283 A | 4/1994 | Conners | |
| 5,306,286 A | 4/1994 | Stack et al. | |
| 5,312,415 A | 5/1994 | Palermo | |
| 5,314,424 A | 5/1994 | Nicholas | |
| 5,318,525 A | 6/1994 | West et al. | |
| 5,320,632 A | 6/1994 | Heidmueller | |
| 5,325,845 A | 7/1994 | Adair | |
| 5,330,442 A | 7/1994 | Green et al. | |
| 5,332,402 A | 7/1994 | Teitelbaum | |
| 5,342,393 A | 8/1994 | Stack | |
| 5,350,397 A | 9/1994 | Palermo et al. | |
| 5,350,399 A | 9/1994 | Erlebacher et al. | |
| 5,359,994 A | 11/1994 | Kreuter et al. | |
| 5,364,351 A * | 11/1994 | Heinzelman | A61M 25/0136 600/585 |
| 5,368,564 A | 11/1994 | Savage | |
| 5,368,601 A | 11/1994 | Sauer et al. | |
| 5,383,886 A | 1/1995 | Kensey et al. | |
| 5,391,182 A | 2/1995 | Chin | |
| 5,403,312 A | 4/1995 | Yates et al. | |
| 5,403,326 A | 4/1995 | Harrison et al. | |
| 5,411,552 A | 5/1995 | Andersen et al. | |
| 5,417,699 A | 5/1995 | Klein et al. | |
| 5,417,700 A | 5/1995 | Egan | |
| 5,423,857 A | 6/1995 | Rosenman et al. | |
| 5,423,858 A | 6/1995 | Bolanos et al. | |
| 5,423,882 A | 6/1995 | Jackman et al. | |
| 5,431,666 A | 7/1995 | Sauer et al. | |
| 5,437,551 A | 8/1995 | Chalifoux | |
| 5,437,681 A | 8/1995 | Meade et al. | |
| 5,445,646 A * | 8/1995 | Euteneuer | A61F 2/95 604/103.02 |
| 5,447,966 A | 9/1995 | Hermes et al. | |
| 5,450,860 A | 9/1995 | O'Connor | |
| 5,456,400 A | 10/1995 | Shichman et al. | |
| 5,456,684 A | 10/1995 | Schmidt et al. | |
| 5,462,527 A | 10/1995 | Stevens-Wright et al. | |
| 5,472,044 A | 12/1995 | Hall et al. | |
| 5,476,470 A | 12/1995 | Fitzgibbons, Jr. | |
| 5,477,856 A | 12/1995 | Lundquist | |
| 5,478,309 A | 12/1995 | Sweezer et al. | |
| 5,478,353 A | 12/1995 | Yoon | |
| 5,487,746 A | 1/1996 | Yu et al. | |
| 5,496,332 A | 3/1996 | Sierra et al. | |
| 5,507,725 A | 4/1996 | Savage et al. | |
| 5,507,755 A | 4/1996 | Gresl et al. | |
| 5,507,757 A | 4/1996 | Sauer et al. | |
| 5,520,701 A | 5/1996 | Lerch | |
| 5,522,873 A | 6/1996 | Jackman et al. | |
| 5,527,313 A | 6/1996 | Scott et al. | |
| 5,527,321 A | 6/1996 | Hinchliffe | |
| 5,527,322 A | 6/1996 | Klein et al. | |
| 5,536,251 A | 7/1996 | Evard et al. | |
| 5,540,705 A | 7/1996 | Meade et al. | |
| 5,542,949 A | 8/1996 | Yoon | |
| 5,554,185 A | 9/1996 | Block et al. | |
| 5,562,678 A | 10/1996 | Booker | |
| 5,569,274 A | 10/1996 | Rapacki et al. | |
| 5,571,085 A | 11/1996 | Accisano, III | |
| 5,571,135 A * | 11/1996 | Fraser | A61F 2/95 606/198 |
| 5,571,137 A | 11/1996 | Marlow et al. | |
| 5,571,215 A | 11/1996 | Sterman et al. | |
| 5,575,802 A | 11/1996 | McQuilkin et al. | |
| 5,582,611 A | 12/1996 | Tsuruta et al. | |
| 5,593,424 A | 1/1997 | Northrup, III | |
| 5,593,435 A | 1/1997 | Carpentier et al. | |
| 5,609,598 A | 3/1997 | Laufer et al. | |
| 5,618,306 A | 4/1997 | Roth et al. | |
| 5,620,452 A | 4/1997 | Yoon | |
| 5,620,461 A | 4/1997 | Muijs Van De Moer et al. | |
| 5,626,588 A | 5/1997 | Sauer et al. | |
| 5,634,932 A | 6/1997 | Schmidt | |
| 5,636,634 A | 6/1997 | Kordis et al. | |
| 5,639,277 A | 6/1997 | Mariant et al. | |
| 5,640,955 A | 6/1997 | Ockuly et al. | |
| 5,649,937 A | 7/1997 | Bito et al. | |
| 5,662,681 A | 9/1997 | Nash et al. | |
| 5,669,917 A | 9/1997 | Sauer et al. | |
| 5,690,671 A | 11/1997 | McGurk et al. | |
| 5,695,504 A | 12/1997 | Gifford, III et al. | |
| 5,695,505 A | 12/1997 | Yoon | |
| 5,702,825 A | 12/1997 | Keita et al. | |
| 5,706,824 A | 1/1998 | Whittier | |
| 5,709,707 A | 1/1998 | Lock et al. | |
| 5,713,910 A | 2/1998 | Gordon et al. | |
| 5,713,911 A | 2/1998 | Racene et al. | |
| 5,715,817 A | 2/1998 | Stevens-Wright et al. | |
| 5,716,367 A | 2/1998 | Koike et al. | |
| 5,718,725 A | 2/1998 | Sterman et al. | |
| 5,719,725 A | 2/1998 | Nakao | |

(56) References Cited

U.S. PATENT DOCUMENTS

| | | |
|---|---|---|
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,280 A * | 11/1999 | Euteneuer ............... A61F 2/95 623/1.1 |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,168,617 B1 * | 1/2001 | Blaeser ............... A61F 2/958 623/1.11 |
| 6,171,320 B1 | 1/2001 | Monassevitch |
| 6,174,322 B1 | 1/2001 | Schneidt |
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,579,279 B1 * | 6/2003 | Rabiner ............ A61M 25/0067 604/528 |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |

(56) References Cited

U.S. PATENT DOCUMENTS

| | | | |
|---|---|---|---|
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,291,168 B2 | 11/2007 | Macoviak et al. |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,637,933 B2 * | 12/2009 | Dwyer ............... A61F 2/95 623/1.11 |
| 7,651,502 B2 | 1/2010 | Jackson |
| 7,655,015 B2 | 2/2010 | Goldfarb et al. |
| 8,070,799 B2 * | 12/2011 | Righini ............... A61F 2/2436 623/2.11 |
| 8,435,279 B2 * | 5/2013 | Beyerlein ........... A61F 2/966 623/1.11 |
| 8,518,106 B2 * | 8/2013 | Duffy ................. A61F 2/2427 623/1.11 |
| 9,011,513 B2 * | 4/2015 | Bialas ................ A61F 2/966 623/1.11 |
| 9,326,875 B2 * | 5/2016 | Shumer ............. A61M 25/0009 |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058951 A1 * | 5/2002 | Fiedler ............... A61F 2/95 606/108 |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0199975 A1 | 10/2003 | Gabbay |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |

(56) References Cited

U.S. PATENT DOCUMENTS

| | | |
|---|---|---|
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0038509 A1 | 2/2005 | Ashe |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0060030 A1 | 3/2005 | Lashinski et al. |
| 2005/0070844 A1* | 3/2005 | Chow ............... A61M 25/0012 604/95.04 |
| 2005/0149014 A1 | 7/2005 | Hauck et al. |
| 2005/0159810 A1 | 7/2005 | Filsoufi |
| 2005/0182475 A1* | 8/2005 | Jen .............................. A61F 2/95 623/1.11 |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0272975 A1* | 12/2005 | McWeeney ........ A61B 1/00071 600/113 |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0030866 A1 | 2/2006 | Schreck |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0200221 A1* | 9/2006 | Malewicz ................ A61F 2/966 623/1.11 |
| 2006/0229708 A1 | 10/2006 | Powell et al. |
| 2006/0252984 A1 | 11/2006 | Randert et al. |
| 2006/0252993 A1* | 11/2006 | Freed ................... A61B 1/0052 600/146 |
| 2006/0271064 A1* | 11/2006 | Agnew .................... A61F 2/95 606/108 |
| 2007/0038293 A1 | 2/2007 | St. Goar et al. |
| 2007/0055289 A1* | 3/2007 | Scouten ................. A61D 3/00 606/130 |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2007/0213812 A1 | 9/2007 | Webler et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0171976 A1* | 7/2008 | Rios .................. A61M 25/0043 604/96.01 |
| 2008/0183194 A1 | 7/2008 | Goldfarb et al. |
| 2008/0195126 A1 | 8/2008 | Solem |
| 2008/0294175 A1 | 11/2008 | Bardsley et al. |
| 2009/0156995 A1 | 6/2009 | Martin et al. |
| 2009/0157162 A1* | 6/2009 | Chow ....................... A61F 2/95 623/1.11 |
| 2009/0163934 A1 | 6/2009 | Raschdorf, Jr. et al. |
| 2009/0163986 A1* | 6/2009 | Tieu ......................... A61F 2/95 623/1.11 |
| 2009/0177266 A1 | 7/2009 | Powell et al. |
| 2009/0182200 A1* | 7/2009 | Golden ............. A61M 25/0043 600/153 |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0121437 A1 | 5/2010 | Subramanian et al. |
| 2010/0262231 A1 | 10/2010 | Tuval et al. |
| 2010/0268204 A1* | 10/2010 | Tieu .................. A61B 17/12022 606/27 |
| 2010/0298929 A1 | 11/2010 | Thornton et al. |
| 2012/0179184 A1 | 7/2012 | Orlov |
| 2012/0265222 A1 | 10/2012 | Gordin et al. |
| 2013/0066341 A1 | 3/2013 | Ketai et al. |
| 2013/0066342 A1 | 3/2013 | Dell et al. |
| 2013/0190772 A1* | 7/2013 | Doerr ...................... A61B 17/86 606/104 |
| 2013/0231735 A1* | 9/2013 | Deem ..................... A61F 2/243 623/2.11 |
| 2013/0304181 A1* | 11/2013 | Green ..................... A61F 2/966 623/1.11 |
| 2013/0304200 A1* | 11/2013 | McLean ................ A61F 2/2427 623/2.18 |
| 2014/0039511 A1 | 2/2014 | Morris et al. |
| 2014/0180124 A1* | 6/2014 | Whiseant ........... A61B 5/02055 600/467 |
| 2014/0200649 A1* | 7/2014 | Essinger ................ A61F 2/2436 623/1.12 |
| 2014/0276913 A1 | 9/2014 | Tah et al. |
| 2014/0277356 A1* | 9/2014 | Shumer ................... A61F 2/966 623/1.12 |
| 2014/0309661 A1* | 10/2014 | Sheps ............... A61M 25/0147 606/130 |
| 2014/0309670 A1 | 10/2014 | Bakos et al. |
| 2014/0350662 A1 | 11/2014 | Vaturi |
| 2014/0358224 A1 | 12/2014 | Tegels et al. |
| 2015/0051698 A1 | 2/2015 | Ruyra Baliarda et al. |
| 2015/0094800 A1 | 4/2015 | Chawla |
| 2015/0119981 A1 | 4/2015 | Khairkhahan et al. |
| 2015/0142100 A1* | 5/2015 | Morriss ................. A61F 2/2418 623/2.4 |
| 2015/0230947 A1 | 8/2015 | Krieger et al. |
| 2015/0257877 A1 | 9/2015 | Hernandez |
| 2015/0366665 A1* | 12/2015 | Lombardi ............. A61F 2/2427 623/2.11 |
| 2016/0015410 A1 | 1/2016 | Asirvatham et al. |
| 2016/0038280 A1* | 2/2016 | Morriss ................. A61F 2/2436 623/2.18 |
| 2016/0045314 A1 | 2/2016 | Keren et al. |
| 2016/0051386 A1* | 2/2016 | Haarmann-Thiemann .................. A61F 2/958 623/1.11 |
| 2016/0116056 A1* | 4/2016 | Geissler .................. F16H 57/12 248/274.1 |
| 2016/0128767 A1* | 5/2016 | Azamian ............ A61B 18/1492 606/41 |
| 2016/0174979 A1 | 6/2016 | Wei |

(56) References Cited

U.S. PATENT DOCUMENTS

| | | | |
|---|---|---|---|
| 2018/0008268 A1 | 1/2018 | Khairkhahan | |
| 2018/0036119 A1 | 2/2018 | Wei et al. | |
| 2018/0125658 A1 | 5/2018 | Prabhu | |

FOREIGN PATENT DOCUMENTS

| | | |
|---|---|---|
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 1230899 | 8/2002 |
| EP | 1674040 | 6/2006 |
| EP | 1935377 | 6/2008 |
| EP | 2005912 | 12/2008 |
| EP | 2641570 | 9/2013 |
| FR | 2768324 | 3/1999 |
| GB | 1598111 | 9/1981 |
| GB | 2151142 | 7/1985 |
| JP | H09253030 | 9/1997 |
| JP | H11089937 | 4/1999 |
| JP | 2000283130 | 10/2000 |
| JP | 2015502548 | 1/2015 |
| WO | WO1981000668 | 3/1981 |
| WO | WO1991001689 | 2/1991 |
| WO | WO1991018881 | 12/1991 |
| WO | WO1992012690 | 8/1992 |
| WO | WO1994018881 | 9/1994 |
| WO | WO1994018893 | 9/1994 |
| WO | WO1995011620 | 5/1995 |
| WO | WO1995015715 | 6/1995 |
| WO | WO1996014032 | 5/1996 |
| WO | WO1996020655 | 7/1996 |
| WO | WO1996022735 | 8/1996 |
| WO | WO1996030072 | 10/1996 |
| WO | WO1997018746 | 5/1997 |
| WO | WO1997025927 | 7/1997 |
| WO | WO1997026034 | 7/1997 |
| WO | WO1997038748 | 10/1997 |
| WO | WO1997039688 | 10/1997 |
| WO | WO1997048436 | 12/1997 |
| WO | WO1998007375 | 2/1998 |
| WO | WO1998024372 | 6/1998 |
| WO | WO1998030153 | 7/1998 |
| WO | WO1998032382 | 7/1998 |
| WO | WO1998035638 | 8/1998 |
| WO | WO1999000059 | 1/1999 |
| WO | WO1999001377 | 1/1999 |
| WO | WO1999007354 | 2/1999 |
| WO | WO1999013777 | 3/1999 |
| WO | WO1999044524 | 9/1999 |
| WO | WO1999066967 | 12/1999 |
| WO | WO2000002489 | 1/2000 |
| WO | WO2000003651 | 1/2000 |
| WO | WO2000003759 | 1/2000 |
| WO | WO2000012168 | 3/2000 |
| WO | WO2000044313 | 8/2000 |
| WO | WO2000059382 | 10/2000 |
| WO | WO2000060995 | 10/2000 |
| WO | WO2001000111 | 1/2001 |
| WO | WO2001000114 | 1/2001 |
| WO | WO2001003651 | 1/2001 |
| WO | WO2001026557 | 4/2001 |
| WO | WO2001026586 | 4/2001 |
| WO | WO2001026587 | 4/2001 |
| WO | WO2001026588 | 4/2001 |
| WO | WO2001026703 | 4/2001 |
| WO | WO2001028455 | 4/2001 |
| WO | WO2001047438 | 7/2001 |
| WO | WO2001049213 | 7/2001 |
| WO | WO2001050985 | 7/2001 |
| WO | WO2001054618 | 8/2001 |
| WO | WO2001056512 | 8/2001 |
| WO | WO2001066001 | 9/2001 |
| WO | WO2001070320 | 9/2001 |
| WO | WO2001089440 | 11/2001 |
| WO | WO2001095831 | 12/2001 |
| WO | WO2001095832 | 12/2001 |
| WO | WO2001097741 | 12/2001 |
| WO | WO2002000099 | 1/2002 |
| WO | WO2002001999 | 1/2002 |
| WO | WO2002003892 | 1/2002 |
| WO | WO2002034167 | 5/2002 |
| WO | WO2002060352 | 8/2002 |
| WO | WO2002062263 | 8/2002 |
| WO | WO2002062270 | 8/2002 |
| WO | WO2002062408 | 8/2002 |
| WO | WO2003001893 | 1/2003 |
| WO | WO2003003930 | 1/2003 |
| WO | WO2003020179 | 3/2003 |
| WO | WO2003028558 | 4/2003 |
| WO | WO2003037171 | 5/2003 |
| WO | WO2003047467 | 6/2003 |
| WO | WO2003049619 | 6/2003 |
| WO | WO2003073910 | 9/2003 |
| WO | WO2003073913 | 9/2003 |
| WO | WO2003082129 | 10/2003 |
| WO | WO2003094801 | 11/2003 |
| WO | WO2003105667 | 12/2003 |
| WO | WO2004004607 | 1/2004 |
| WO | WO2004006810 | 1/2004 |
| WO | WO2004012583 | 2/2004 |
| WO | WO2004012789 | 2/2004 |
| WO | WO2004014282 | 2/2004 |
| WO | WO2004019811 | 3/2004 |
| WO | WO2004030570 | 4/2004 |
| WO | WO2004037317 | 5/2004 |
| WO | WO2004045370 | 6/2004 |
| WO | WO2004045378 | 6/2004 |
| WO | WO2004045463 | 6/2004 |
| WO | WO2004047679 | 6/2004 |
| WO | WO2004062725 | 7/2004 |
| WO | WO2004082523 | 9/2004 |
| WO | WO2004082538 | 9/2004 |
| WO | WO2004093730 | 11/2004 |
| WO | WO2004103162 | 12/2004 |
| WO | WO2004112585 | 12/2004 |
| WO | WO2004112651 | 12/2004 |
| WO | WO2005002424 | 1/2005 |
| WO | WO2005018507 | 3/2005 |
| WO | WO2005027797 | 3/2005 |
| WO | WO2005032421 | 4/2005 |
| WO | WO2005062931 | 7/2005 |
| WO | WO2005112792 | 12/2005 |
| WO | WO2006037073 | 4/2006 |
| WO | WO2006105008 | 10/2006 |
| WO | WO2006105009 | 10/2006 |
| WO | WO2006113906 | 10/2006 |
| WO | WO2006115875 | 11/2006 |
| WO | WO2006115876 | 11/2006 |
| WO | WO 2011102968 | 8/2011 |
| WO | WO2013049734 | 4/2013 |
| WO | WO2013103934 | 7/2013 |
| WO | WO2015020971 | 2/2015 |
| WO | WO2018026445 | 2/2018 |
| WO | WO2018089617 | 5/2018 |
| WO | WO2018094042 | 5/2018 |

OTHER PUBLICATIONS

Agricola et al., "Mitral Valve Reserve in Double Orifice Technique: an Exercise Echocardiographic Study," Journal of Heart Valve Disease, 11(5):637-643 (2002).

Alfieri et al., "An Effective Technique to Correct Anterior Mitral Leaflet Prolapse," J. Card Surg., 14:468-470 (1999).

Alfieri et al., "Novel Suture Device for Beating Heart Mitral Leaflet Approximation," Annals of Thoracic Surgery, 74:1488-1493 (2002).

Alfieri et al., "The double orifice technique in mitral valve repair: a simple solution for complex problems," Journal of Thoracic and Cardiovascular Surgery, 122:674-681 (2001).

Alfieri et al., "The edge to edge technique," The European Association for Cardio-Thoracic Surgery 14th Annual Meeting, Oct. 7-11, 2000, Book of Proceedings.

(56) References Cited

OTHER PUBLICATIONS

Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Ali Khan et al, Blade Atrial Septostomy: Experience with the First 50 Procedures, Cathet. Cardiovasc. Diagn., Aug. 1991, pp. 257-262, vol. 23.
Arisi et al., "Mitral Valve Repair with Alfieri Technique in Mitral Regurgitation of Diverse Etiology: Early Echocardiographic Results," Circulation Supplement II, 104(17):3240 (2001).
Alvarez et al, Repairing the Degenerative Mitral Valve: Ten to Fifteen-year Follow-up, Journal of Thoracic Cardiovascular Surgery, Aug. 1996, pp. 238-247, vol. 112, No. 2.
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dec et al, Idiopathic Dilated Cardiomyopathy, The New England Journal of Medicine, Dec. 8, 1994, pp. 1564-1575, vol. 331, No. 23.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. For Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].

Fucci et al, Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).

(56) References Cited

OTHER PUBLICATIONS

Maisano et al, The Edge-to-edge Technique: A Simplified Method to Correct Mitral Insufficiency, Eur. J. Cardiothorac. Surg., Jan. 14, 1998, pp. 240-246, vol. 13.
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
McCarthy et al, Tricuspid Valve Repair with the Cosgrove-Edwards Annuloplasty System, Ann. Thorac. Surg., Jan. 16, 1997, pp. 267-268, vol. 64.
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001).[Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al, Clinical Use of Blade Atrial Septostomy, Circulation, 1978, pp. 600-608, vol. 58, No. 4.
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al, Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge to-Edge Repair of Mitral Regurgitation," Journal of Heart Valve Disease, 11:810-822 (2002).
U.S. Appl. No. 14/216,813, Mar. 9, 2017, Office Action.
U.S. Appl. No. 14/216,813, Dec. 15, 2017, Office Action.
U.S. Appl. No. 14/216,813, Apr. 6, 2018, Office Action.
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 15/347,543, Dec. 28, 2018, Office Action.
U.S. Appl. No. 14/216,813, Jan. 31, 2019, Office Action.
U.S. Appl. No. 15/347,543, Mar. 18, 2019, Notice of Allowance.

* cited by examiner

CARDIAC IMPLANT DELIVERY SYSTEM

CROSS-REFERENCE TO RELATED APPLICATIONS

N/A

BACKGROUND

Heart valve diseases are often treated by replacing the malfunctioning heart valve with a replacement valve implant. Heart valves that are replaced with replacement valve implants include the mitral valve, the aortic valve, the tricuspid valve, and the pulmonary valve, with the mitral valve and the aortic valve being the most commonly replaced valves. Typically, heart valves are replaced to address undesirable stenosis (i.e., narrowing) of a valve, or to correct regurgitation caused by an improperly functioning valve. One problem often requiring a valve replacement is mitral valve regurgitation. When the mitral valve is in a regurgitant condition, the mitral valve does not properly close, allowing oxygenated blood to flow backwards in the heart. As a result, blood is not moved as efficiently through the heart and the rest of the body, often leaving people with symptoms including shortness of breath, irregular heartbeats, and chest pain.

Before a replacement valve implant can be deployed, it must be properly positioned with respect to a targeted implanting location. Often, heart valve replacement procedures include a sternotomy performed in an open-heart-surgery. Less invasive procedures seek to access the target area by passing a catheter system through a patient's vasculature. When the vascular system of the patient is used, a catheter system may be inserted into an artery or vein percutaneously or through a small incision in the patient's body to allow the catheter system to be threaded through the patient's body to the target location. However, precise delivery of replacement heart valves remains a challenge due to the structure at or near the target location or due to the particular demands of the implant to be delivered. Additionally, some procedures may require a particular alignment and/or orientation of the implant to enable proper placement of the implant.

Further, while some catheter guiding systems adapted for use in other interventional cardiac procedures are available, there exist additional challenges that limit effective use of such catheter guiding systems for delivery and deployment of replacement valve implants. For example, compared to many other interventional cardiac procedures, the delivery and deployment of a replacement heart valve implant requires higher precision in positioning of the implant with respect to the targeted treatment area. In addition, replacement heart valve implants are often inherently bulkier than other interventional implant devices, increasing difficulties in steering and positioning of the replacement valve. Further, heart valve target areas can often be difficult to reach, requiring a relatively tortuous path and/or relatively high turn curvatures to obtain proper alignment and orientation of the delivered implant.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to delivery systems configured for delivering an interventional device to a targeted treatment area within a body. Some embodiments are directed to delivery systems configured for delivering a replacement heart valve implant to a targeted heart valve within a body. Some embodiments include a steerable catheter having a proximal end and a distal end, where the steerable catheter has a diameter within a range of 0.20 to 0.50 inches, or 0.33 to 0.43 inches. Some embodiments include an interventional device delivery system positioned within the steerable catheter and configured to be translatable within the steerable catheter. Some embodiments include a handle coupled to the proximal end of the catheter, the handle having one or more controls and one or more corresponding steering mechanisms enabling steering of the steerable catheter.

In some embodiments, the delivery system includes one or more control wires, each control wire being coupled to a control of the handle at one end and to the distal end of the steerable catheter at the other end such that tensioning of the control wire can actuate corresponding deflection in the steerable catheter. In some embodiments, the one or more control wires are formed from a material having an ultimate tensile strength greater than that of 304 stainless steel. In some embodiments, the one or more control wires are formed from a material having an ultimate tensile strength within a range of 600 to 2300 MPa, or 700 to 1500 MPa. In some embodiments, the one or more control wires are formed from a titanium or titanium alloy.

In some embodiments, a handle of the delivery system includes a rotatable control operatively coupled to a control wire tensioning wheel through a gear assembly, the gear assembly being arranged so that rotation of the wire tensioning wheel relative to rotation of the rotatable control is reduced by a factor greater than 8. In some embodiments, a steerable catheter includes a plurality of cuts arranged to enable one or more of preferential bending or increased flexibility of the steerable catheter.

In some embodiments, a handle of the delivery system includes a motor configured to provide motor-assisted tensioning of one or more of the control wires. In certain embodiments, the handle includes a rotatable control operatively coupled to a control wire tensioning wheel such that rotation of the rotatable control causes rotation of the control wire tensioning wheel so as to tension the one or more control wires. In some embodiments, the motor is configured to assist in rotating the control wire tensioning wheel according to rotation of the rotatable control.

In some embodiments, a delivery system configured for delivering a replacement heart valve to a targeted heart valve within the body includes a catheter configured to house a deployable replacement valve, the catheter having a proximal end and a distal end. The system also includes a distal tip enclosing a distal section of the replacement valve. The distal tip is distally translatable relative to the replacement valve. The system also includes a sheath enclosing a proximal section of the replacement valve. The sheath is proximally translatable relative to the replacement valve. The distal tip is distally translatable upon subjection to a distally oriented hydraulic force to deploy the distal section of the replacement valve, and the sheath is proximally translatable to deploy the proximal section of the replacement valve.

In some embodiments, a delivery system configured for delivering a replacement heart valve to a targeted heart valve within the body includes a catheter configured to house a deployable replacement valve, the catheter having a proximal end and a distal end. The system also includes a sheath enclosing the replacement heart valve. The sheath defines an inter-luminal space through which at least a portion of a shaft extends. The shaft includes a plurality of fluid ports enabling the passage of fluid into the inter-luminal space so as to cause the sheath to translate proximally relative to the replacement heart valve to deploy the replacement heart valve.

In some embodiments, a delivery system configured for delivering a replacement heart valve to a targeted heart valve within the body includes a catheter configured to house a deployable replacement valve, the catheter having a proximal end and a distal end. The system also includes a tether detachably coupled to the replacement heart valve, the tether and the replacement heart valve forming a magnetic coupling upon passage of electric current through the tether. The tether is selectively detachable from the replacement heart valve upon cessation of the electric current.

In some embodiments, a delivery system configured for delivering a replacement heart valve to a targeted heart valve within the body includes a catheter configured to house a deployable replacement valve, the catheter having a proximal end and a distal end. The system also includes a tether detachably coupled to the replacement heart valve, the tether including a meltable portion and a heat-transmitting portion. The transmission of heat through the heat-transmitting portion causes sufficient melting of the meltable portion to decouple the tether from the replacement heart valve.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

One or more embodiments described herein relate to replacement heart valve delivery systems. Certain embodiments described herein are adapted to enable effective delivery and deployment of a replacement heart valve at a targeted area of a patient. As described herein, at least some of the delivery systems include one or more features or components which enhance the effectiveness of the delivery systems when used in applications for delivering and deploying a replacement heart valve. In some embodiments, one or more components or features of a replacement valve delivery system distinguish the replacement valve delivery system from other delivery systems typically used for delivery of other interventional cardiac devices, and thereby offer advantages and benefits not obtainable by the other delivery systems, particularly in implementations of delivering and deploying a replacement heart valve.

Throughout this disclosure, many examples are described in the context of delivery and deployment of a replacement mitral valve. One of skill in the art will understand, however, that the described components, features, and principles may be applied in other similar implementations. For example, at least some of the embodiments described herein may be utilized for delivery and deployment of a pulmonary, aortic, or tricuspid replacement valve, or even another interventional implant, such as a chordae replacement, occlusion device, annuloplasty ring, or other interventional tool used in a repair or replacement procedure.

As used herein, the terms "guide catheter," "delivery catheter," "steerable catheter," and the like are used interchangeably to refer to a catheter configured to be selectively steerable in response to actuation of one or more operator controls. The terms "sleeve," "delivery sleeve," and the like are also used herein to refer to a catheter structure configured to be positioned within an outer catheter. Typically, in embodiments including a sleeve, an outer catheter is referred to as the "guide catheter," while the inner catheter is referred to as the "sleeve." It will be understood, however, that a catheter and a sleeve may be configured similarly. Accordingly, features and components related to a sleeve may be applied to a catheter, and vice versa.

Figure 1:
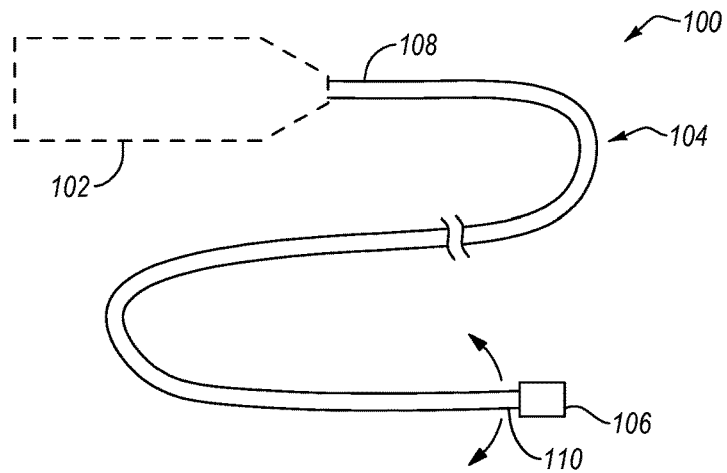
FIG. 1 illustrates an exemplary delivery system for delivering an interventional device to a targeted area within a body.

FIG. 1 illustrates a delivery system 100 having a handle 102, a catheter 104, and an interventional device 106, such as a replacement valve. The handle 102 is connected to the proximal end 108 of the catheter 104 and may be configured to be operatively connected to one or more lumens of the catheter 104 to provide movement control over the catheter 104. The interventional device 106 may be connected to a distal end 110 of the catheter 104. The one or more lumens of the catheter 104 may also allow the handle 102 to be operatively connected with the interventional device 106. In some embodiments, the interventional device 106 is a replacement heart valve, such as a replacement mitral valve configured to function as the mitral valve of a patient's heart once positioned and implanted in the mitral valve annulus of the patient's heart. In some embodiments, at least one of the lumens of the catheter 104 is configured to enable deflection of the distal end 110 of the catheter 104 in response to manipulation of the handle 102.

Figure 2:
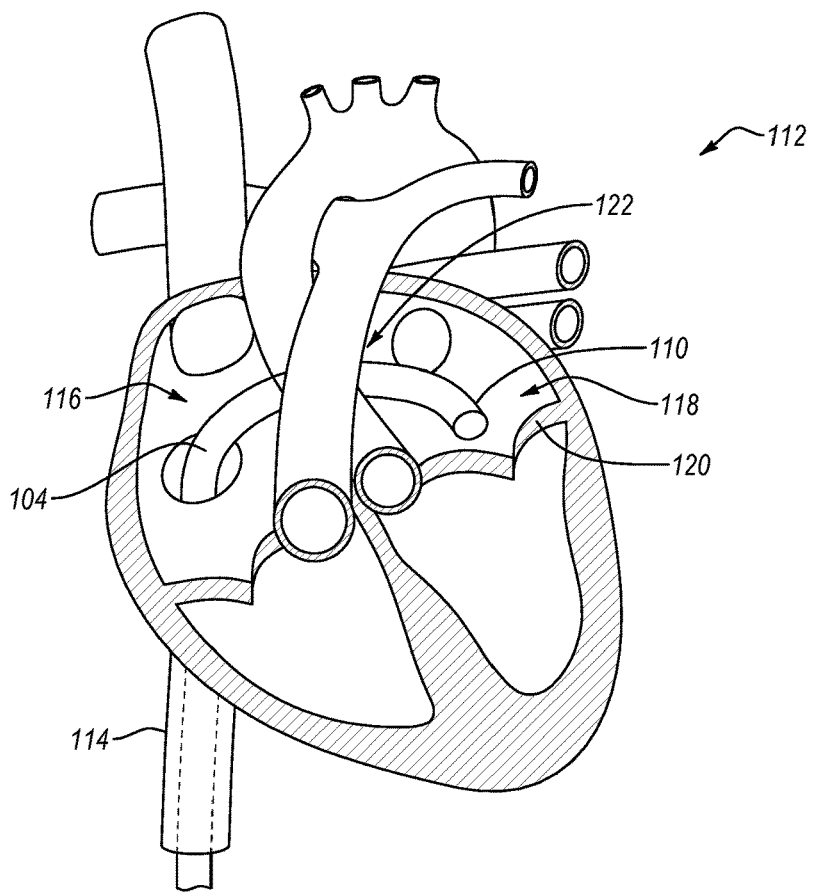
FIG. 2 illustrates a procedure wherein a guide catheter is positioned at a mitral valve of a patient's heart.

FIG. 2 illustrates a schematic representation of a patient's heart 112 and a medical procedure that may be conducted using a delivery system according to the present disclosure. A delivery catheter 104 may be inserted into the patient's vasculature and directed to the inferior vena cava 114. The catheter 104 is passed through the inferior vena cava 114 toward the heart 112. Upon entering the heart 112 from the inferior vena cava 114, the catheter 104 enters the right atrium 116. For procedures associated with the mitral valve 120, such as deployment of a replacement mitral valve, the catheter 104 must further pass into the left atrium 118. As shown, the catheter 104 may reach the left atrium 118 through a puncture 122 in the intra-atrial septum. In other implementations, such as for procedures associated with a tricuspid valve, the catheter 104 may be passed through the inferior vena cava 114 into the right atrium 116, where it may then be positioned and used to perform the procedure related to the tricuspid valve. As described above, although many of the examples described herein are directed to the mitral valve and particularly to delivery and deployment of a replacement mitral valve, one or more of the embodiments described herein may be utilized in other cardiac procedures. For example, one or more embodiments described herein may be utilized for delivery and deployment of a replacement tricuspid valve.

To perform a maneuver such as that shown in FIG. 2, the distal end 110 of the catheter 104 may be deflected and steered by tensioning one or more control wires positioned inside the catheter 104. Precise control of the distal end 110 of the catheter 104, as provided by one or more of the embodiments described herein, may allow for smaller punctures in the intra-atrial septum and/or more reliable positioning of a replacement valve or other interventional device. In some embodiments, a replacement valve is coupled to the distal end 110 of the catheter 104. Additionally, or alternatively, a replacement valve and/or one or more other interventional devices may be passed through the catheter 104 as needed to complete a procedure. For example, the catheter 104 may be brought to a desired position and orientation, after which one or more interventional devices may be passed through the catheter 104 and guided to the targeted treatment site.

Figure 3:
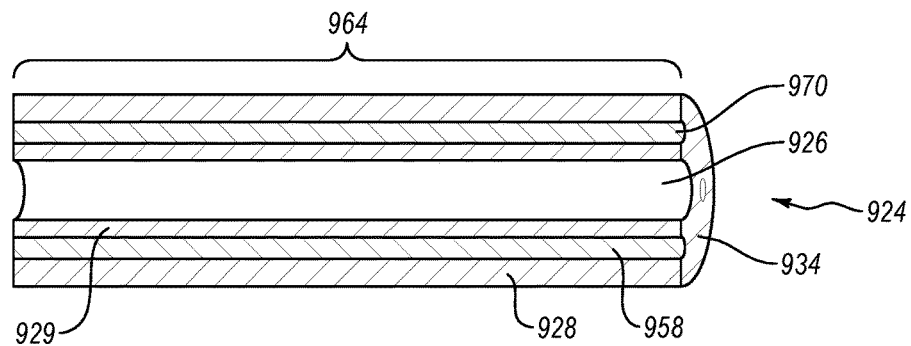
FIGS. 3-5 illustrate an exemplary guide catheter having one or more control wires enabling steering of the guide catheter.
Figure 4:
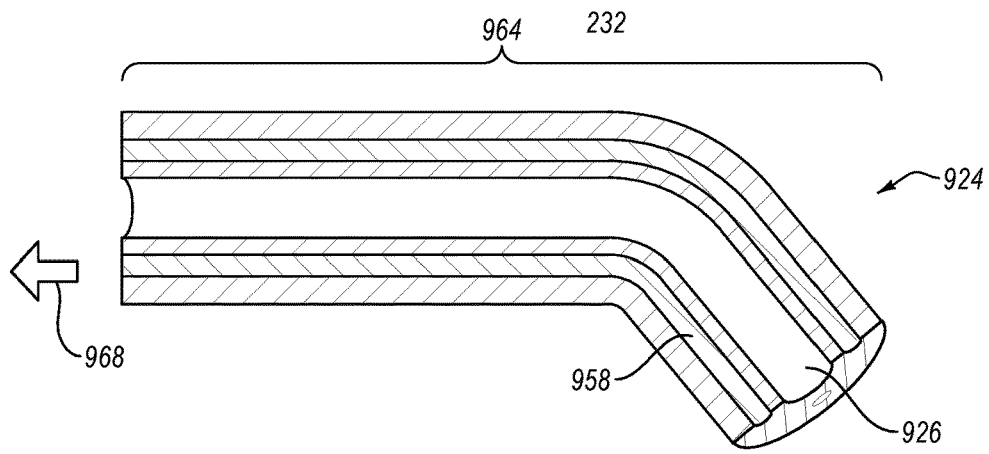
Figure 5:
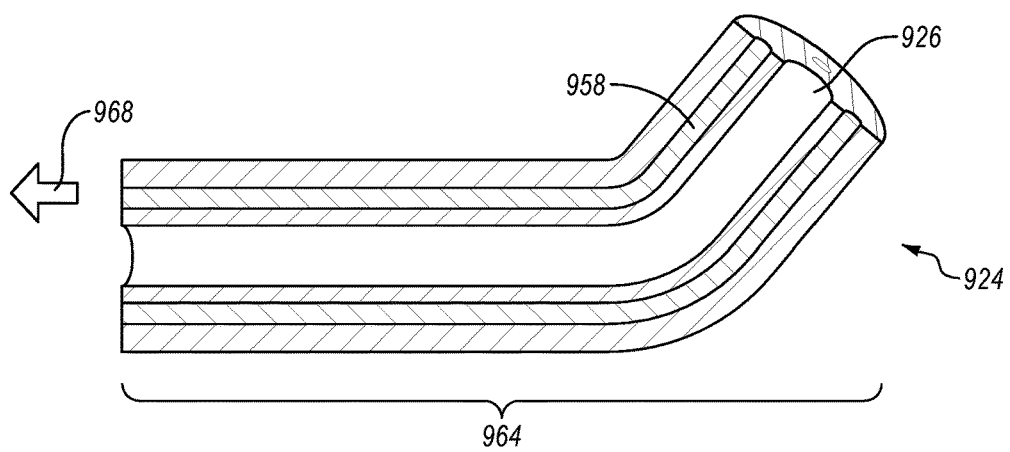

FIGS. 3-5 illustrate cross-sectional views of a distal section 964 of a catheter 924 according to one embodiment of the disclosure. The illustrated catheter 924 may be utilized in a delivery catheter system such as the delivery catheter system 100 illustrated in FIG. 1 and/or in the procedure illustrated in FIG. 2). A body 934 of the catheter 924 extends from a proximal end (not shown) to the illustrated distal section 964. The catheter 924 includes a major lumen 926 and one or more minor lumens 970 disposed between the major lumen 926 and an outer circumferential wall 928.

The minor lumens 970 provide conduits through the catheter 924 for control wires 958. In some embodiments, the control wires 958 allow a handle at the proximal end of the catheter 924 to control position and/or steering of the catheter 924. In some embodiments, one or more control wires 958 may be used for controlling an interventional device at the distal end of the catheter 924. For example, one or more control wires 958 may connect to a replacement heart valve to allow control over decoupling, unsheathing, and/or deploying of the replacement valve.

In preferred embodiments, the one or more control wires 958 are formed from a material having greater tensile strength than stainless steel (e.g., 304 stainless steel). For example, the some embodiments include one or more control wires formed from titanium. Control wires having these levels of tensile strength are particularly beneficial in applications involving delivery and deployment of replacement valves, where higher forces are often required to steer relatively larger catheters and/or relatively bulkier replacement valves (e.g., relatively larger/bulkier as compared to components used in a typical valve repair procedure). In some embodiments, one or more control wires are configured to exhibit an ultimate tensile strength of greater than about 400, 500, 600, 700, or 800 MPa. In some embodiments, upper ranges for ultimate tensile strength are about 1200, 1500, 1800, 2100, or 2300. For example, some embodiments include one or more control wires having an ultimate tensile strength within a range of about 400 to 2300 MPa, or about 500 to 2100 MPa, or about 600 to 1800 MPa, or about 700 to about 1500 MPa.

In some embodiments, the catheter 924 is substantially cylindrical (e.g., has a substantially circular transverse cross-section). In other embodiments, the catheter 924 has a transverse cross-section that is square, triangular, pentagonal, octagonal, other polygonal, elliptical, regular, irregular, or combinations thereof. The major lumen 926 may be centrally located within the catheter 924 such that the major lumen 926 shares a common longitudinal axis with the catheter 924. In other embodiments, the major lumen 926 is non-coaxially disposed within the catheter 924 (e.g., the major lumen 926 is offset from the longitudinal axis of the catheter 924). In some embodiments, a catheter includes a plurality of major lumens. For example, a plurality of major lumens may be arranged around the longitudinal axis of the catheter 924.

In some embodiments, the major lumen 926 is substantially circular in transverse cross-section, while in other embodiments, the major lumen 926 may have other cross-sectional shapes, such as a transverse cross-section that is square, triangular, pentagonal, octagonal, other polygonal, elliptical, regular, irregular, or combinations thereof. In embodiments with a plurality of major lumens, the major lumens may be the same in size and shape or may have different sizes and/or shapes. For example, a first major lumen may have a circular cross-section and a second major lumen may have a crescent-shaped cross-section that complimentarily partially surrounds the first major lumen.

The catheter 924 may have a plurality of minor lumens 970. In some embodiments, the minor lumens 970 are distributed equally about the longitudinal axis of the catheter 924. For example, the minor lumens 970 may be distributed about the longitudinal axis at equal intervals according to the quantity of the minor lumens 970. Four minor lumens 970 may be distributed at equal 90° intervals. Three minor lumens 970 may be distributed at equal 120° intervals, etc. In other embodiments, at least two of the minor lumens 970 are disposed substantially opposite one another (e.g., the at least two minor lumens exhibit inversion symmetry about the longitudinal axis of the catheter 924).

The major lumen 926 and minor lumens 970 may be integrally formed with a body 934 of the catheter 924. The body 934 may be made of or include a variety of flexible body materials such as thermoplastic elastomers (TPE). The body 934 may be formed of one or more of a variety of materials along one or more segments or layers. Example materials include polyurethane, polyether block amides (e.g., as sold under the trade name PEBAX®), nylon, polyester, polyethylene, polyimide, polyethylenetelephthalate (PET), polyetheretherketone (PEEK), and combinations thereof. In addition, the catheter 924 may be reinforced with a variety of structures, such as metal braids or coils. Such reinforcements may be along the entire length of the catheter 924 or in various segments.

In some embodiments, the body 934 may be a polyether block amide (PEBA). The body 934 may have a constant durometer or may have varying durometer along the longitudinal length of the body 934. For example, the body 934 may be made of or include a body material having a durometer of 35 D to 55 D. In another example, the body 934 may be made of or include a body material that has a durometer of about 45 D. In at least one embodiment, the body material may include a PEBAX® polyether block amide material, such as PEBAX® 4533 and/or PEBAX® 3533.

In some embodiments, particularly embodiments suitable for delivery of a replacement valve, the catheter 924 has a diameter ranging between any two upper and lower values including 0.15 inches, 0.20 inches, 0.25 inches, 0.30 inches, 0.35 inches, 0.40 inches, 0.45 inches, and 0.50 inches. In embodiments with a non-circular body (e.g., an octagonal body), the diameter may be approximated as the average distance from a longitudinal axis of the non-circular body to an outer surface of the catheter. In preferred embodiments, the catheter 924 has a diameter less than about 0.43 inches (33 French), or even more preferably, less than about 0.37 inches (28 French). While such sizes will typically allow delivery of the catheter 924 across the septum (as shown in FIG. 2) without the need for subsequent repair of the septum, the sizes are larger than catheter sizes in other interventional procedures (e.g., a catheter diameter of about 0.12 inches for a valve repair procedure).

Such relatively larger sizes are often required to enable delivery of replacement valves to a targeted treatment area. These larger sized catheters, replacement valves, and/or other components can add challenges to an interventional procedure. For example, steering of bulkier and/or heavier catheters and other components while maintaining needed precision can be increasingly difficult. One or more of the embodiments described herein provide features enabling control and precision for steering such guide catheters and/or delivering and deploying a replacement valve device.

In some embodiments, the major lumen 926 has a diameter such that the ratio of the diameter of the major lumen 926 to the diameter of the catheter 924 is within a range having upper and lower values including any of 0.400, 0.425, 0.450, 0.475, 0.500, 0.525, or any value therebetween. For example, the major lumen to catheter diameter ratio may be within a range of 0.400 to 0.525. In another example, the major lumen to catheter diameter ratio may be within a range of 0.450 to 0.500, or about 0.475.

As shown, the major lumen 926 and the one or more minor lumens 970 may be separated by a portion of the body 934 that defines an inner circumferential wall 929. The inner circumferential wall 929 is configured to be strong enough to prevent puncture and/or rupture of either the major lumen 926 or a minor lumen 970 into the other. For example, the inner circumferential wall 929 may have a thickness such that a ratio of the thickness to the diameter of the catheter 924 is within a range having upper and lower values including any of 0.100, 0.110, 0.120, 0.130, 0.140, 0.150, values greater than 0.150, or any value therebetween. For example, the wall thickness to catheter ratio may be within a range of 0.100 and 0.150. In another example, the wall thickness to catheter ratio may be within a range of 0.110 and 0.140. In yet another example, the wall thickness to catheter ratio may be 0.120.

The catheter 924 may have any length appropriate to access the desired target area of a patient's body. In some embodiments, the catheter 924 has a length of about 40 to 80 inches, or about 50 to 70 inches, or about 60 inches. In some embodiments, the catheter 924 includes PEBAX 3533 in the distal portion 964 and PEBAX 4533 in the intermediate portion 962 and proximal portion 960. The body 934 may have a substantially constant outer diameter along the length of the catheter 924. In some embodiments, the body 934 may have different handling characteristics along the length thereof while maintaining a constant outer diameter. For example, different sections of the catheter 924 may be formed from different materials to provide different flexibilities and/or other characteristics. In other embodiments, the distal portion 964 and/or other portions may taper toward a proximal or distal end. A tapered distal portion 964 may reduce overall material in the catheter 924 at a given longitudinal position, tuning a flexibility profile of the catheter 924.

The illustrated catheter 924 incorporates control wires 958 to provide control over the position and/or deflection of the catheter 924. FIG. 3 depicts the distal portion 964 of the catheter 924 with a pair of control wires 958 each disposed within a minor lumen 970. The control wires 958 may connect to the catheter 924 at or near the distal end 910 and extend proximally through the minor lumens. In other embodiments, the control wires 958 may connect to the distal portion 964 of the body 934 not at the distal end 910. As described herein, the control wires 958 may convey forces applied at a proximal end (not shown) of the control wires 958 to the distal end 966 of the control wires 958. The distal end 966 of the control wires 958 may then convey the force to the distal portion 964 of the shaft 924.

FIGS. 4 and 5 respectively depict a proximal force 968 applied to oppositely disposed control wires 958. The control wires 958 are connected to the distal end of the catheter 924. The proximal force 968 moves the corresponding control wire 958 proximally. The movement of the control wire 958 applies a torque to the distal end of the catheter 924 to rotate and/or deflect the distal end, providing an arcuate delivery path through the major lumen 926. The major lumen 926 may be positioned using the movement of the control wires 958 to precisely deliver interventional devices (such as interventional device 106 described in relation to FIG. 1, which may be a replacement valve implant) or other devices, tools, implants, or objects to the targeted area of a patient's body.

Accordingly, by selectively applying tension to the one or more control wires 958, the distal end of the catheter 924 may be curved in the direction of the control wires 958, as depicted. In the illustrated embodiment, the opposed control wires 958 enable at least the distal section 964 of the catheter 924 to be steered in opposite directions. This provides a means of correcting or adjusting a curvature. For example, if tension is applied to one control wire to create a curvature, the curvature may be lessened by applying tension to the opposite control wire. Other embodiments may include a single control wire, or may include more than two control wires. In addition, control wires and associated lumens may be placed in any arrangement, singly or in pairs, symmetrically or nonsymmetrically, to enable desired curvature capabilities. Control wires 958 may be fixed at any location along the length of the catheter 924 by any suitable method, such as gluing, tying, soldering, and the like. When tension is applied to a control wire 958, the curvature forms from the point of attachment of the control wire 958 toward the proximal direction. Typically, control wires are attached near the distal end of the catheter 924.

Figure 6:
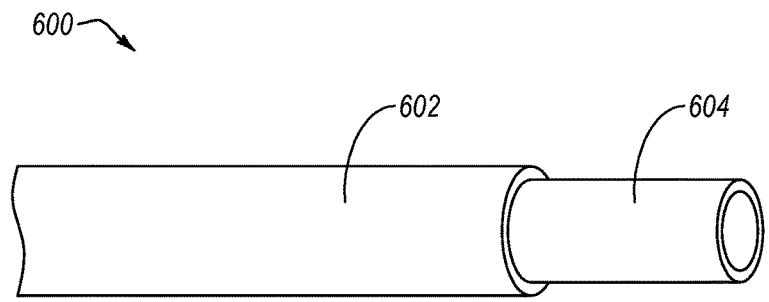
FIG. 6 illustrates an exemplary delivery system including a guide catheter and a sleeve positioned within the guide catheter.

FIG. 6 illustrates an embodiment of a delivery system 600 including an outer catheter 602 and an inner sleeve 604 translatable within the outer catheter 602. One or both of the outer catheter 602 and the inner sleeve 604 may be configured as the catheter 924 described in relation to FIGS. 3-5, and the description related to FIGS. 3-5 is incorporated into the description of the embodiment of FIG. 6. For example, one or both of the depicted outer catheter 602 and inner sleeve 604 may be configured to be steerable (e.g., using one or more control wires and corresponding minor lumens, as described). Steering of the catheter system 600 may therefore be achieved by adjusting the tension of one or more control wires to curve the outer catheter 602 and/or sleeve 604 in the direction of the tension. Additionally, or alternatively, one or more of the outer catheter 602 or the sleeve 604 may be precurved to provide a desired angling for properly traversing a patient's vasculature in the context of a particular procedural approach.

For example, precurvature or steering of the outer catheter 602 can direct the distal end of the outer catheter 602 to form a first curve, while precurvature or steering of the sleeve 602 can direct the distal end of the sleeve 602 to form a second curve. Typically, the first curve differs from that of the second curve so that together the curves form a compound curve. Often, at least for a procedure targeting a mitral valve using a transfemoral approach, the primary curve has a radius of curvature in the range of 0.8 to 1.0 inches and the secondary curve has a radius of curvature in the range of 0.050 to 0.750 inches. Advancement of an interventional device (e.g., a replacement valve) through the sleeve 604 thereby guides the device through the resulting compound curve, and enables the interventional device to be delivered to the targeted treatment area in a desired orientation. The interventional device may then be actuated, deployed, and/or released.

Figure 7:
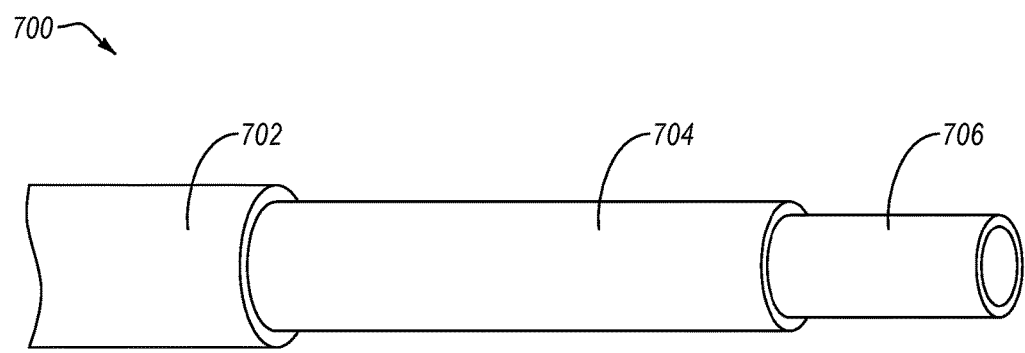
FIG. 7 illustrates an exemplary delivery system including a guide catheter, a sleeve positioned within the guide catheter, and a valve delivery system positioned within the sleeve.

FIG. 7 illustrates an embodiment of a delivery system 700 including an outer catheter 702, an inner sleeve 704, and a valve delivery system 706 translatable within the inner sleeve 704. The valve delivery system 706 is configured to house and delivery a replacement valve to a targeted area of a patient. The outer catheter 702 and inner sleeve 704 may be configured as the outer catheter 602 and inner sleeve 604 described in relation to FIG. 6. Although the depicted delivery system 700 includes both an outer catheter 702 and a sleeve 704, other embodiments may omit the outer catheter 702 or the sleeve 704. For example, some embodiments include a single steerable catheter and a valve delivery system 706 translatable within the steerable catheter.

Figure 8:
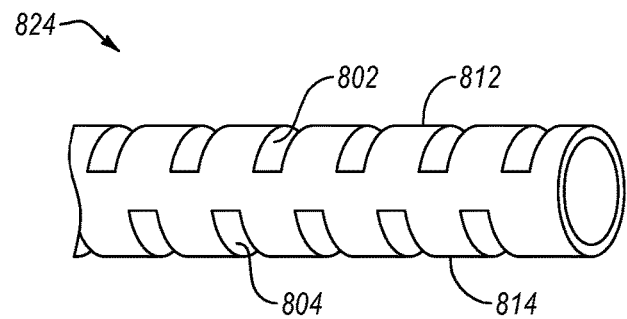
FIG. 8 illustrates a guide catheter having a plurality of cuts to enhance the axial flexibility of the guide catheter.
Figure 9:
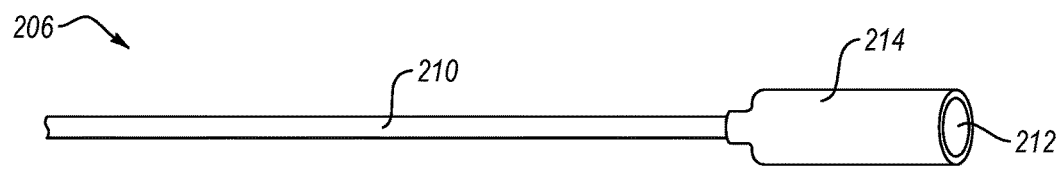
FIG. 9 illustrates an exemplary valve delivery system having a sheath for housing a replacement valve.

FIG. 8 illustrates an embodiment of a delivery catheter 824 configured to have preferential bending and/or increased axial flexibility. The illustrated delivery catheter 824, and similar embodiments, may be utilized as an outer catheter and/or as a sleeve in a delivery system such as those described in relation to FIGS. 6 and 7, for example. As shown, the delivery catheter 824 includes a plurality of slits or cuts arranged so as to allow preferential bending of the delivery catheter 824 in one or more directions. For example, the illustrated embodiment includes a first set of cuts 802 arranged on a first side 812 of the catheter 824 and a second set of cuts 804 arranged opposite the first set of cuts 802 on a second side 814 of the catheter 824, leaving a longitudinal spine 806 running on sides adjacent to the sets of cuts 802 and 804.

In the illustrated embodiment, the first and second sets of cuts 802 and 804 enable the catheter 824 to be preferentially bent in directions corresponding to the sides on which the cuts are arranged. For example, the catheter 824 may be bent in a direction corresponding to the first side 812 or in a direction corresponding to the second side 814 with less force than other bending directions. Such preferential bending can beneficially allow the catheter 824 to be manipulated to a desired position and/or orientation with minimal force, as compared to a similar catheter not having preferential bending, without overly reducing the structural integrity of the catheter 824 to a detrimental degree.

These benefits may be particularly useful in implementations where procedural demands require relatively larger diameter catheters, bulkier interventional devices, and/or other features that tend to increase the difficulty in steering and/or manipulating a guide catheter. For example, some procedures for delivering and deploying a replacement heart valve may require larger catheters and/or one or more bulkier devices as compared to other interventional procedures, such as interventional heart valve repair procedures. Embodiments including preferential bending features may be utilized in such valve replacement procedures in order to increase the maneuverability of the guide catheter 824 while maintaining structural integrity and other features and components of delivery catheters as described herein.

The arrangement of cuts shown in FIG. 8 is one example of a cutting arrangement that may be utilized to provide preferential bending. Other embodiments may include different arrangements or patterns of cuts. For example, some embodiments may include cuts on only one side of the catheter so as to limit preferential bending substantially to one direction. Other embodiments may include a cut pattern that is equally circumferentially arranged so that bending is equally available for any direction, and is easier as compared to a catheter having no cuts. Some embodiments may include different cutting patters in different sections or lengths of the catheter. In some embodiments, a cutting pattern can alternate from section to section along at least a given length of the catheter, and/or can include different circumferential offsets from section to section (e.g., 10, 30, 45, 60, or 90 degrees).

FIGS. 9 to 13D illustrate exemplary embodiments of valve delivery systems (i.e., interventional device delivery systems) that may be utilized as, or in conjunction with, one or more of the catheters and/or delivery systems described herein. The valve delivery system 206 illustrated in FIG. 9 includes a catheter or shaft 210 extending between a proximal end (not shown) and a distal end 212. A sheath 214 is disposed at the distal end 212, and is configured to house a replacement valve. For example, a replacement valve or a component of a replacement valve may be housed within the sheath 214 in a crimped or compressed configuration. During deployment, the shaft 210 may be translated relative to the sheath 214 so as to move the replacement valve or replacement valve component out of the sheath, where it may move toward an open or expanded configuration. For example, the replacement valve or valve component may be advanced out of the sheath 214 (e.g., through a pushing motion of the shaft 210) and/or may be released by withdrawing the sheath 214 proximally relative to the shaft 210.

In some embodiments, the replacement valve is deployed using one or more of a hydraulic force (e.g., transmitted through one or more lumens of the shaft and/or catheter), an electrical signal (e.g., an electrical switch or electrically actuated mechanism), or a magnetic force (e.g., a magnetic coupling between the shaft or other tether and the replacement valve) to advance the replacement valve out of the sheath and/or withdraw the sheath from the replacement valve.

Figure 10A:
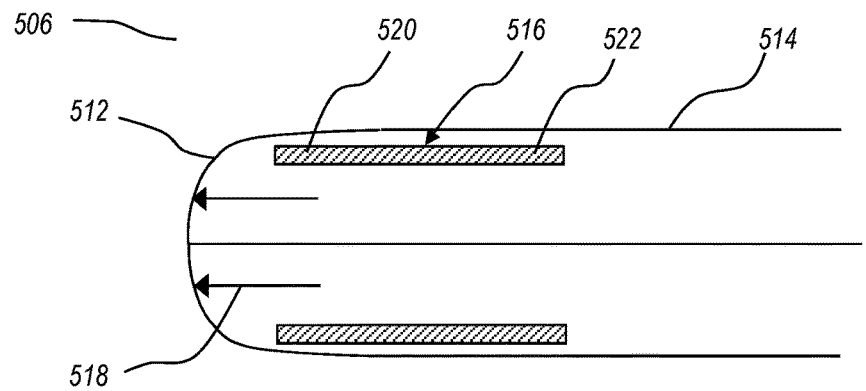
FIGS. 10A-10C illustrate a valve delivery system configured to utilize a hydraulic force to partially deploy a replacement valve.
Figure 10B:
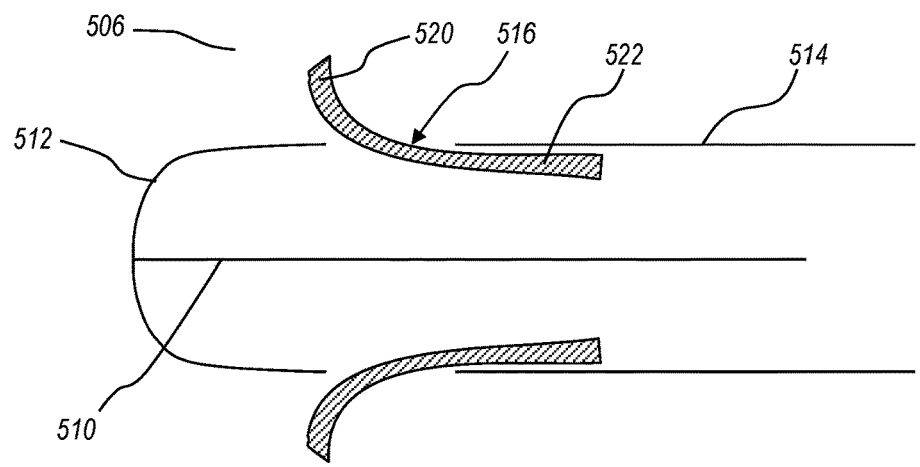
Figure 10C:
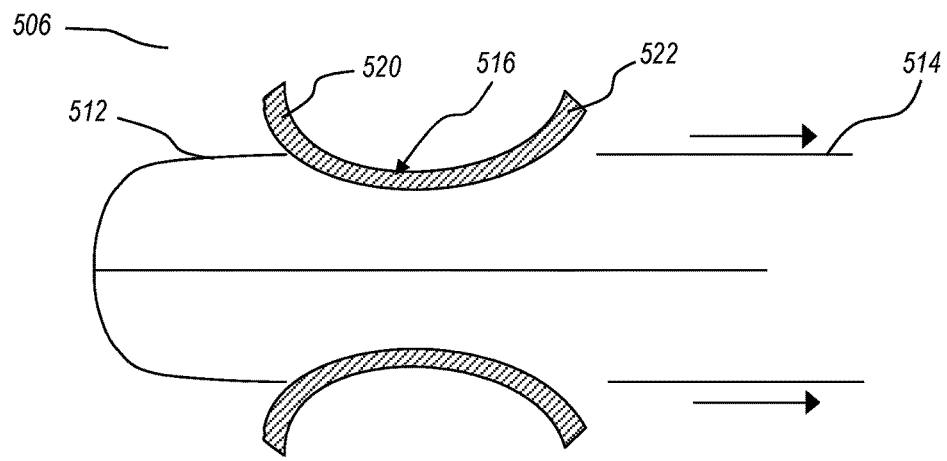

FIGS. 10A to 10C illustrate cross-sectional views of an embodiment of a valve delivery system 506 configured to utilize a hydraulic force to actuate deployment of a replacement valve 516 housed within the valve delivery system 506. In this embodiment, a distal section 520 of the replacement valve 516 is encompassed by a distal tip 512 (i.e., a first sheath portion), and a proximal section 522 of the replacement valve 516 is encompassed by a proximal sheath 514 (i.e., a second sheath portion. As shown in FIG. 10A, fluid may be routed toward the distal tip 512 of the system in order to induce a hydraulic force against the distal tip 512, as indicated by arrows 518. As shown in FIG. 10B, the hydraulic force causes the distal tip 512 (and the shaft 510 to which it is joined) to move distally relative to the replacement valve 516 and the proximal sheath 514. This causes the distal section 520 of the replacement valve 516 to expand/deploy, while the proximal section 522 of the replacement valve 516 remains in a collapsed position within the proximal sheath 514. As shown in FIG. 10C, the proximal sheath 514 may then be retracted proximally so as to deploy the proximal section 522 of the replacement valve 516.

The deployment mechanisms and multi-step deployment process illustrated by FIGS. 10A to 10C can provide a number of advantages. In some implementations, the distal section 520 may be first deployed and positioned on a first side of a targeted heart valve. Because the replacement valve 516 has not yet been fully deployed, further positioning and fine-tuning of device orientation relative to the targeted valve is more readily performed. Upon achieving a suitable position, the proximal section 522 may then be deployed on a second side of the targeted heart valve. For example, in a mitral valve replacement procedure using a transfemoral approach, the device may be routed through the inferior vena cava into the right atrium, through the septum, and into the left atrium superior to the targeted mitral valve (see the approach illustrated in FIGS. 23 and 24). The device can be positioned across the mitral valve plane such that the distal section 520 is deployed on the ventricular side of the valve. After properly positioning the partially deployed valve, the proximal section 522 may then be deployed on the atrial side of the valve. Alternatively, the proximal section 522 may be deployed first by translating sheath 514, followed by deployment of the distal section 520 by moving the distal tip 512.

In a further benefit, the ability to use separate deployment mechanisms for deploying separate sections of the replacement heart valve (e.g., hydraulically moving the distal tip 512 to unsheathe the distal section 520 and retracting the sheath 514 to uncover the proximal section 522) allows differentiated control over different deployment steps in the process. In this manner, the replacement valve 516 is less likely to be inadvertently fully deployed when only a partial deployment step was intended. In contrast, a single mechanism deployment involves higher risk of inadvertent deployment caused by mechanical malfunction (e.g., a retracting sheath slips too far and deploys more of the valve than intended) or operator mistake (e.g., an operator manually pulls the sheath too far back).

The embodiment illustrated by FIGS. 10A to 10C provides for differentiated deployment (i.e., using different mechanisms) of separate sections of the replacement valve 516. In other embodiments, the valve delivery system 506 is configured so that the distal tip 512 sheaths the entirety of the replacement valve 516 (and the proximal sheath 514 may be omitted). In such an embodiment, the replacement valve 516 may be fully deployed upon application of the hydraulic force 518 to the distal tip 512, and associated distal movement of the distal tip 512 relative to the replacement valve 516.

Figure 11A:
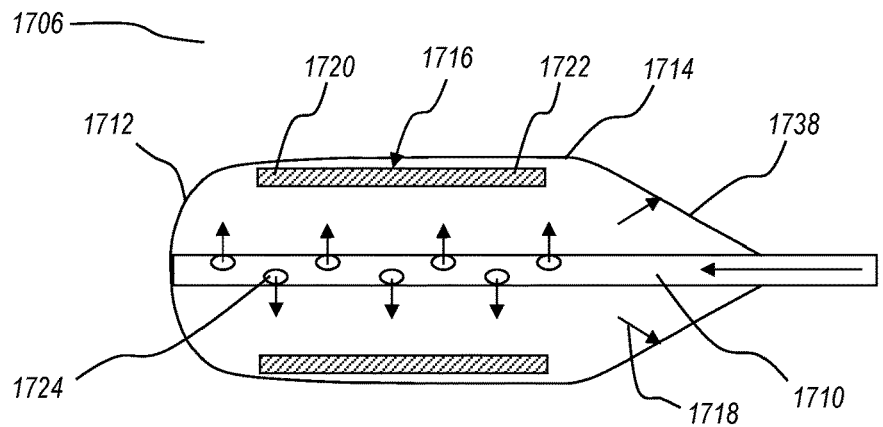
FIGS. 11A-11C illustrate an embodiment of a valve delivery system configured to utilize a hydraulic force to fully deploy a replacement valve.
Figure 11B:
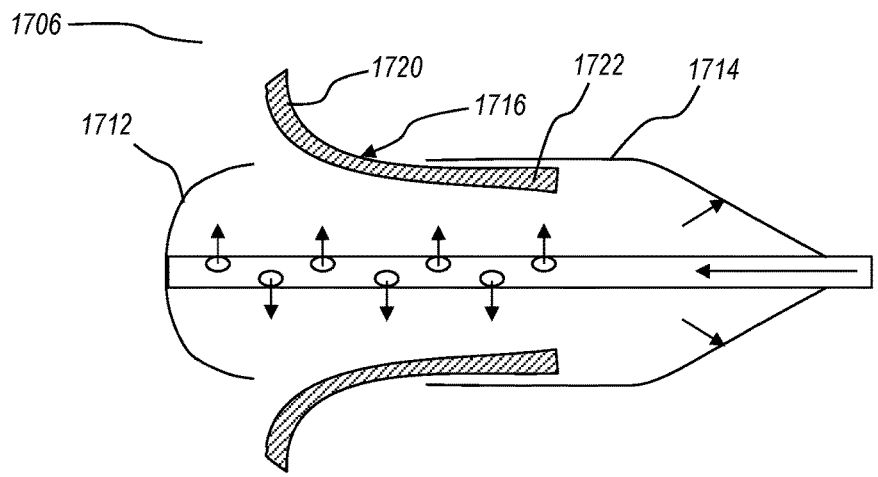
Figure 11C:
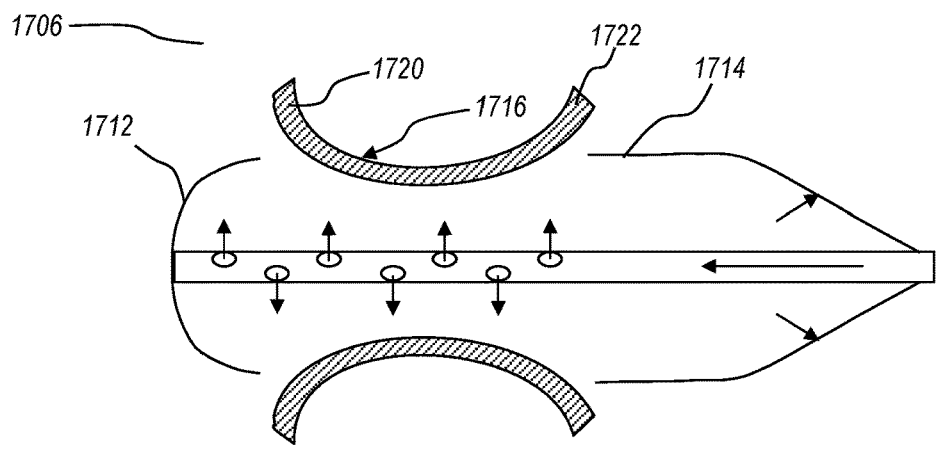

FIGS. 11A to 11C illustrate another embodiment of a valve replacement system 1706 configured to utilize a hydraulic force to actuate deployment of a replacement valve 1716 housed within the delivery system 1706. In this embodiment, a shaft 1710 disposed within a sheath 1714 is provided with one or more fluid ports 1724. The shaft 1710 is configured to be capable of delivering a fluid to the illustrated ports 1724 so that the fluid may be directed into the inter-luminal space defined by the sheath 1714 and the distal tip 1712. As indicated by arrows 1718, the fluid, when sufficiently injected, provides a hydraulic force acting against the sheath 1714. As shown, the sheath 1714 is configured with a proximal wall 1738 that defines the proximal extent of the inter-luminal space. As fluid is injected or passed into the inter-luminal space, the proximal wall 1738 provides a surface for the resulting fluid pressure to act against to move the sheath 1714 proximally away from the replacement valve 1716.

As shown in FIG. 11B, as the sheath 1714 begins to translate proximally, a distal section 1720 of the replacement valve 1716 is deployed. As shown in FIG. 11C, further injection of fluid can cause further corresponding movement of the sheath 1714 so as to deploy the proximal section 1722 of the replacement valve 1716 and complete the valve deployment. In alternative implementations, the proximal section 1722 may be deployed by manually retracting the sheath 1714, in addition to or in the alternative to using further hydraulic force.

Figure 12A:
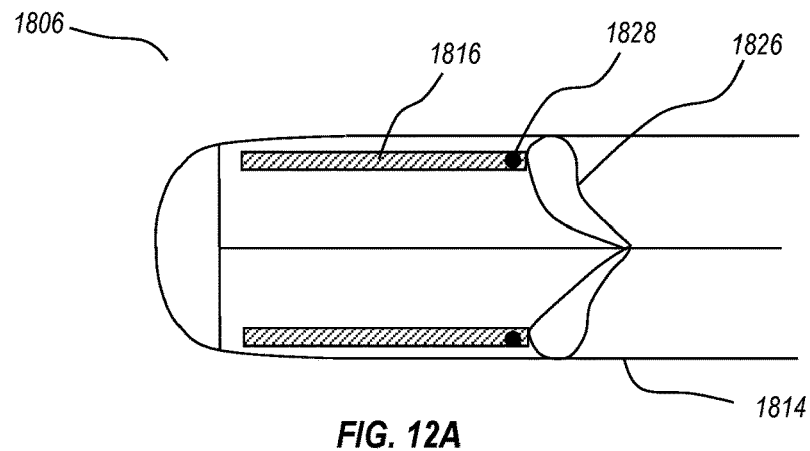
FIGS. 12A-12C illustrate a valve delivery system including an electromagnetic tether detachably coupled to a replacement valve.
Figure 12B:
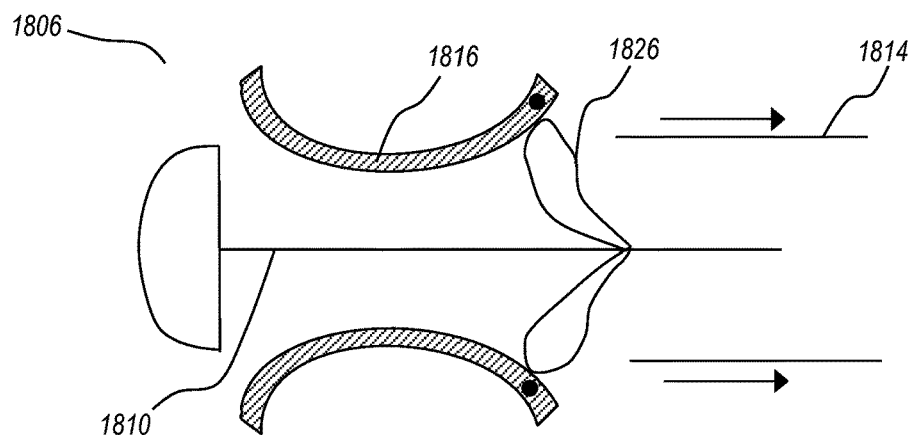
Figure 12C:
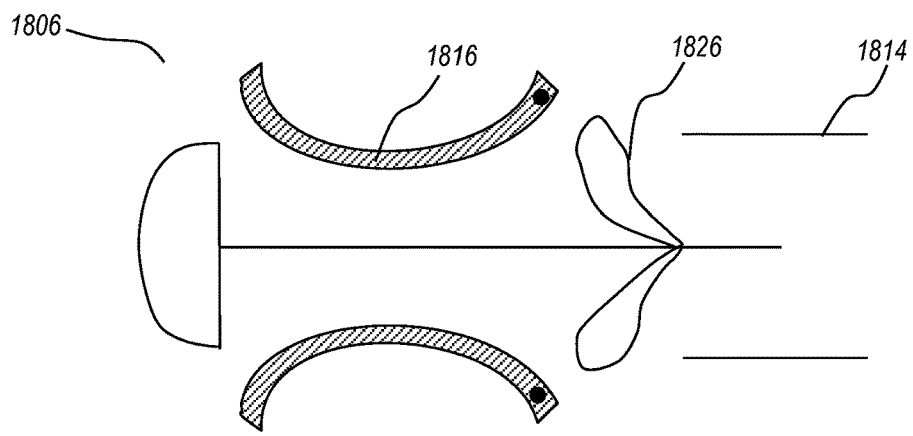

FIGS. 12A to 12C illustrate another embodiment of a valve delivery system 1806 configured to use electromagnetic functionality for deployment of a replacement valve 1816 housed within the valve delivery system 1806. In this embodiment, the replacement valve 1816 is housed by a sheath 1814. A proximal section of the replacement valve 1816 is coupled to an electromagnetic tether 1826 (e.g. an electrically conductive wire/coil structure). In alternative embodiments, the tether 1826 may be coupled to other portions of the replacement valve 1816, in addition to or in the alternative to the proximal section of the valve. At least at the points of the replacement valve 1816 where the tether 1826 contacts the valve 1816, the valve 1816 includes magnetic couplings 1828 (e.g., magnetic beads). The tether 1826 is configured to be electrically conductive such that by passing electric current through the tether, the tether 1826 induces a magnetic field sufficient to couple the tether 1826 to the magnetic couplings 1828 of the valve 1816.

As shown in FIG. 12B, proximal withdrawal of the sheath 1814 (and/or distal extension of the shaft 1810 and valve 1816 relative to the sheath 1814) allows the valve 1816 to expand/deploy. In this position, the replacement valve 1816 is beneficially still held by the tether 1826, allowing an operator to assess positioning of the replacement valve 1816, make adjustments as needed, re-sheath the valve 1816 if orientation is unsatisfactory, or perform other maneuvers before decoupling the valve 1816. As shown in FIG. 12C, the valve 1816 may then be decoupled from the tether 1826 by lowering or turning off the current supply to the tether 1826, thereby breaking the magnetic bond with the valve 1826.

Figure 13A:
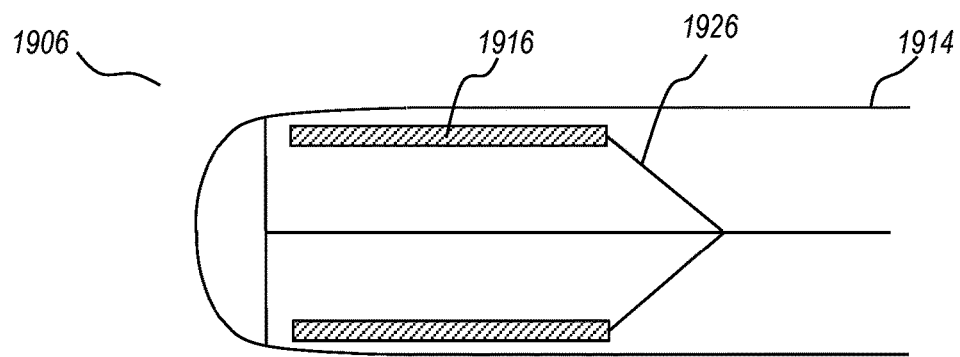
FIGS. 13A-13D illustrate a valve delivery system including a tether coupled to the replacement valve and detachable form the replacement valve upon the application of heat.
Figure 13B:
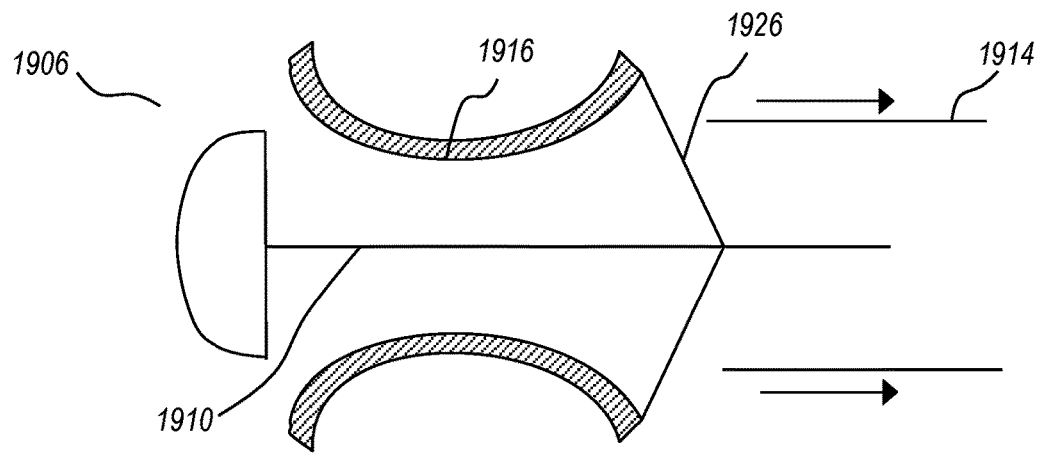
Figure 13C:
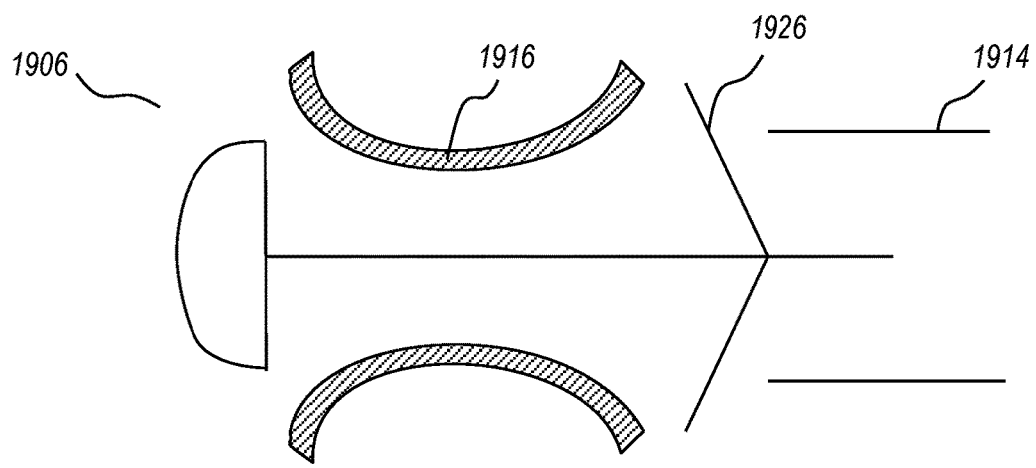

FIGS. 13A to 13C illustrate another embodiment of a valve delivery system 1906 configured to use a releasable tether for deployment of a replacement valve 1916 housed within the valve delivery system 1906. In this embodiment, the replacement valve 1916 is housed by a sheath 1914. A proximal section of the replacement valve 1916 is coupled to a releasable tether 1926. In alternative embodiments, the tether 1926 may be coupled to other portions of the replacement valve 1916, in addition to or in the alternative to the proximal section of the valve. In this embodiment, the tether 1926 is formed at least partly from a meltable material that allows the tether 1926 to be decoupled from the replacement valve 1916 upon melting of the tether 1926.

As shown in FIG. 13B, proximal withdrawal of the sheath 1914 (and/or distal extension of the shaft 1910 and valve 1916 relative to the sheath 1914) allows the valve 1916 to expand/deploy. In this position, the replacement valve 1916 is beneficially still held by the tether 1926, allowing an operator to assess positioning of the replacement valve 1916, make adjustments as needed, re-sheath the valve 1916 if orientation is unsatisfactory, or perform other maneuvers before decoupling the valve 1916. As shown in FIG. 13C, the valve 1916 may then be decoupled from the tether 1926 by applying heat to the tether 1926 to melt the connection between the tether 1926 and the valve 1916, thereby releasing the valve 1916.

Figure 13D:
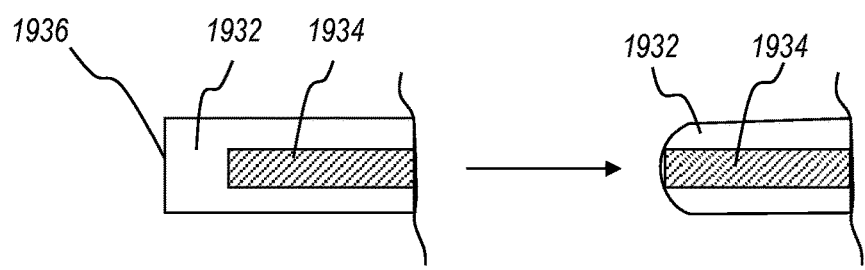

FIG. 13D illustrates a detailed cross-sectional view of a distal section of the tether 1926. The distal end 1936 of the tether 1926 attaches to the replacement valve 1916 to join the tether 1926 to the valve 1916. As shown, the tether 1926 may include a meltable (e.g., polymeric) portion 1932 in association with a heat transmitting (e.g., metallic) portion 1934. In the illustrated embodiment, the meltable portion 1934 is formed as a polymer encasement covering the metallic portion 1934 and extending at least to the distal end 1936 of the tether 1926. Upon the application of heat through the metallic portion 1934 (e.g., through conduction and/or through passage of electrical current) at least the distal end 1936 melts sufficiently to disrupt the connection between the distal end 1936 of the tether 1926 and the replacement valve 1916.

Figure 14:
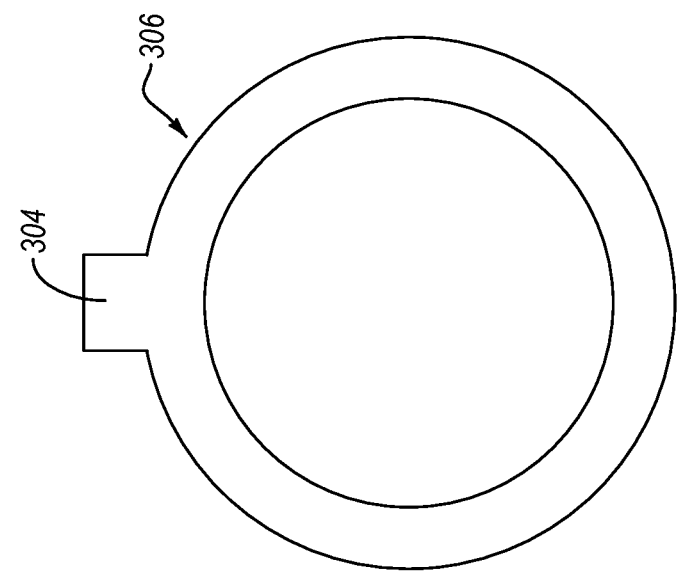
FIG. 14 illustrates a cross-sectional view of a guide catheter and valve delivery system including a rotational locking mechanism for locking rotation of the valve delivery system with respect to the guide catheter.
Figure 14:
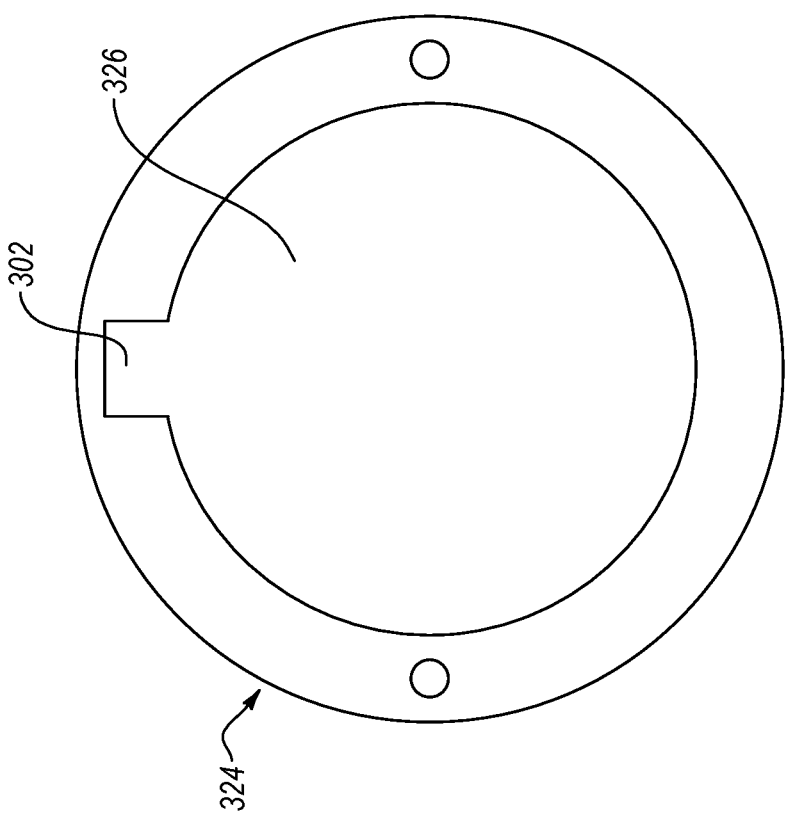

FIG. 14 illustrates transverse cross-sectional views of embodiments of a delivery catheter 324 and a valve delivery system 306 (e.g., a shaft section of the valve delivery system) showing a rotational keyway locking mechanism configured to maintain rotational alignment of the valve delivery system 306 with respect to the delivery catheter 324. The delivery catheter 324 may include one or more features or components of any of the other delivery catheters and/or sleeves described herein, and the valve delivery system 306 may include one or more features or components of any of the other valve delivery systems described herein.

As shown, the delivery catheter 324 includes a major lumen 326 formed with a notch 302. The notch 302 is configured to match and align with a corresponding extension 304 of the valve delivery system 306 such that when the valve delivery system 306 is aligned within the delivery catheter 324, the extension 304 at least partially extends into the notch 302 to lock rotation of the valve delivery system 306 with respect to the delivery catheter 324. The illustrated embodiment includes a single notch and corresponding extension. Other embodiments may include other arrangements of notches and extensions. For example, two, three, four, or more pairs of corresponding notches and extensions may be included, which may be symmetrically or asymmetrically radially positioned around a longitudinal axis of the delivery catheter 324 and/or valve delivery system 306.

Embodiments utilizing a rotation-locking mechanism, such as the illustrated embodiment, may be particularly useful in implementations where a replacement valve to be delivered and deployed is not radially symmetrical. For example, a replacement valve having a "D" shape or other non-symmetrical shape requires precise rotational alignment and orientation with respect to a targeted treatment site in addition to other positioning requirements. Locking rotation of the valve delivery system 306 to the guide catheter 324 enables rotational control of the valve delivery system 306 to be handled through manipulation and control of the delivery catheter 324.

Figure 15:
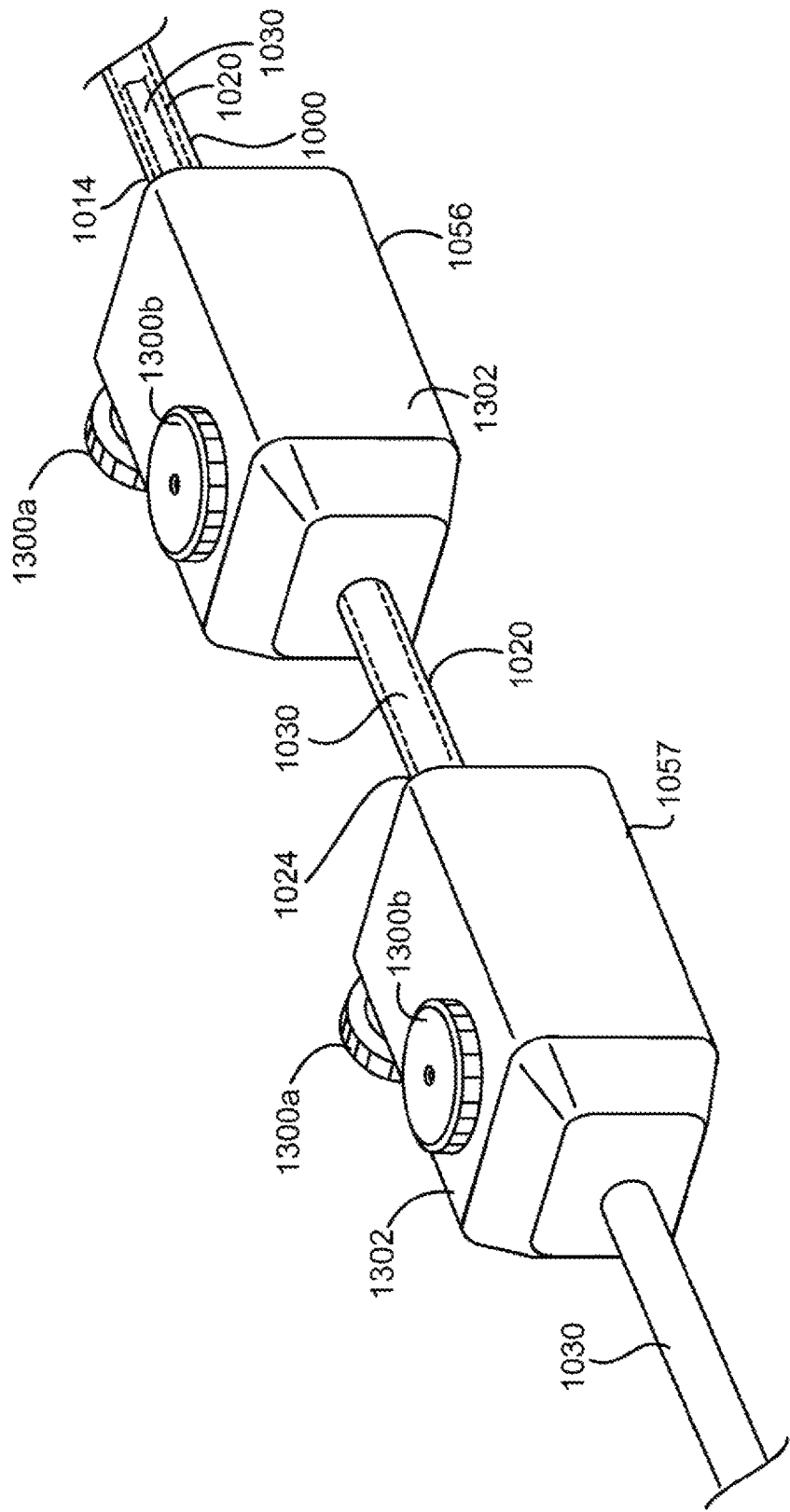
FIGS. 15-17 illustrate an exemplary handle assembly showing steering mechanisms and controls.
Figure 16:
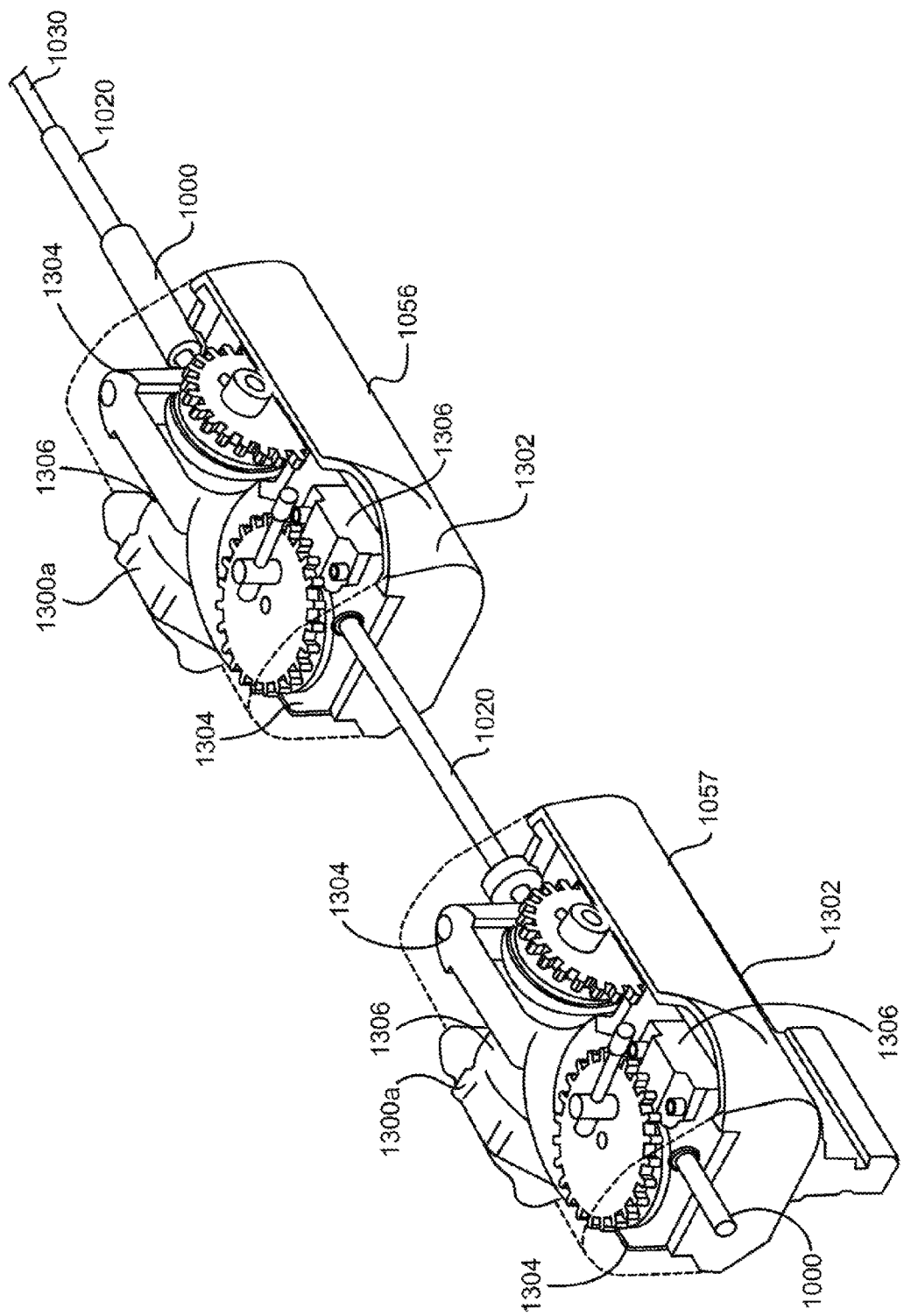
Figure 17:
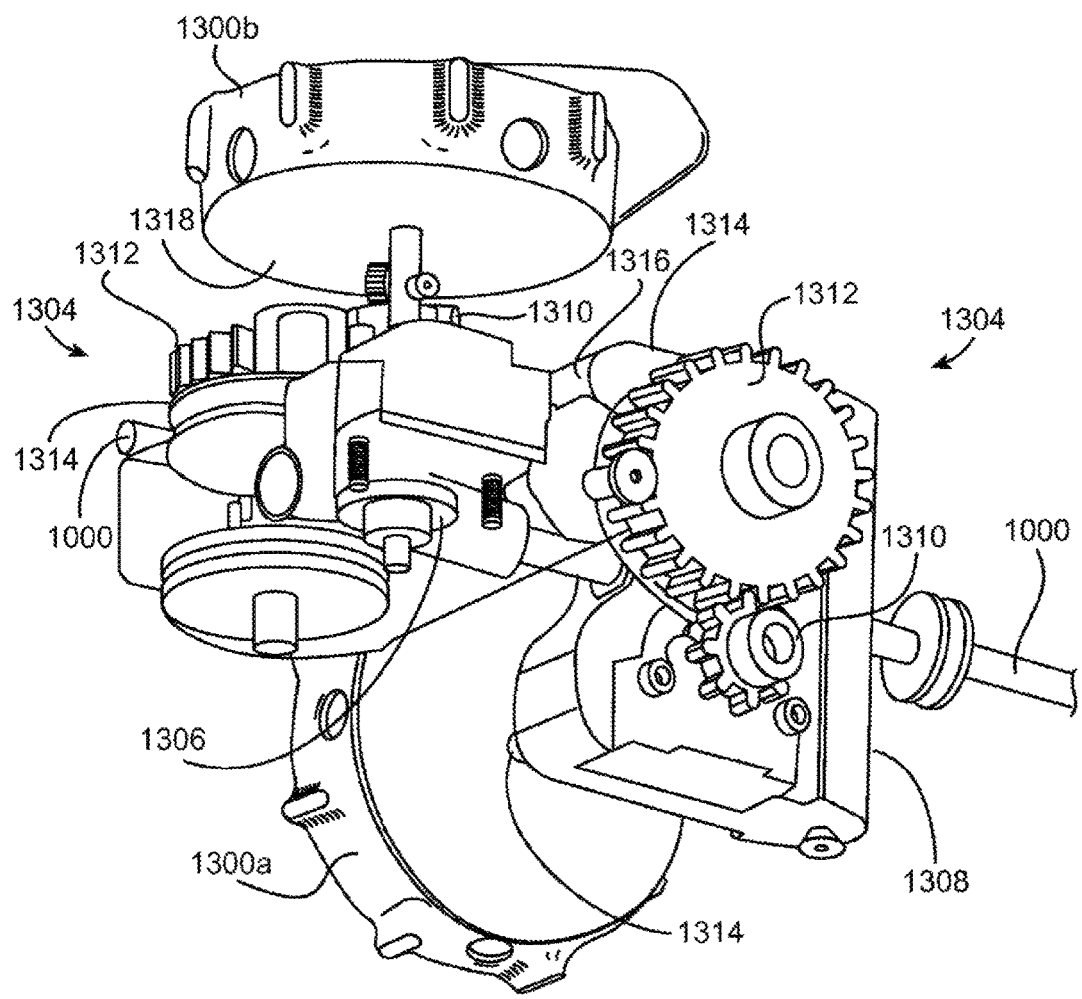

FIGS. 15-17 illustrate one embodiment of a catheter handle system. In some embodiments, one or more of the illustrated handles 1056 and 1057 may replace or may be utilized as the handle 102 of the delivery system 100 of FIG. 1. In the illustrated embodiment, handle 1056 is attached to the proximal end 1014 of outer catheter 1000 and handle 1057 is attached to the proximal end 1024 of sleeve 1020. Sleeve 1020 is inserted through handle 1056 and is positioned within outer catheter 1000. In this embodiment, valve delivery system 1030 is also included and is inserted through the handle 1057 and positioned within the sleeve 1020. In this embodiment, the handles 1056 and 1057 are each included to provide independent control of the outer catheter 1000 and sleeve 1020, respectively. In other embodiments, such as where a sleeve or outer catheter are omitted and/or only one guiding structure is included, the handle 1056 or handle 1057 may be omitted accordingly.

In the illustrated embodiment, each handle 1056 and 1057 includes steering controls in the form of rotatable knobs 1300*a* and 1300*b* coupled to a handle housing 1302. Steering knobs 1300*a* are disposed on a side of the housing 1302 and steering knobs 1300*b* are disposed on a face of the housing 1302. Other embodiments may include one or more differently arranged steering knobs.

FIG. 16 illustrates the handles 1056 and 1057 with a portion of the housing 1302 removed to reveal interior components. Each of the illustrated steering knobs includes a hard stop gear assembly 1304 and a friction assembly 1306. Tension is applied to one or more control wires by action of the hard stop gear assembly 1304 to form a curve in a corresponding catheter. Tension is maintained by the friction assembly 1306.

FIG. 17 illustrates another view of steering mechanisms that may be utilized within a handle (e.g., handle 1056 or 1057). As shown, steering knob 1300*a* is attached to a hard stop gear assembly 1304 and a friction assembly (not in view), and steering knob 1300*b* is attached to a hard stop gear assembly 1304 and a friction assembly 1306. In the illustrated embodiment, steering knobs 1300*a* and 1300*b* are configured similarly and are each coupled to similar sets of steering mechanisms. Description relating to one steering knob therefore applies to another unless specifically stated otherwise.

Steering knob 1300*a* is attached to a knob post 1318 which passes through a base 1308, terminating in a first gear wheel 1310. The first gear wheel 1310 engages a second gear wheel 1312. Rotation of the steering knob 1300a rotates the knob post 1318 and first gear wheel 1310, which in turn rotates the second gear wheel 1312. Rotation of the second gear wheel 1312 applies tension to one or more control wires extending through an associated catheter 1000 (e.g., by wrapping the one or more control wires around a disk 1314 (i.e., control wire tensioning wheel) that rotates with the second gear wheel 1312, as explained in more detail below).

The illustrated embodiment includes a gearing configuration having a second gear wheel 1312 that is larger than the first gear wheel by a factor of about 4. Some embodiments are arranged with different gear ratios. For example, in some circumstances, it may be desirable to provide greater rotation of the second gear wheel 1312, and therefore greater movement of the one or more corresponding control wires, for a given degree of rotation of the knob 1300a. In such embodiments, the gear ratio between the second gear wheel 1312 and the first gear wheel 1310 may be less than 4, such as about 1 to 3.5. In some embodiments, the first gear wheel 1310 may be larger than the second gear wheel 1312. For example, the first gear wheel 1310 may be larger than the second gear wheel 1312 by a factor of about 1.5 to 5 to provide even finer control of the catheter 1000 for a given rotation of the knob 1300a.

In other embodiments, the second gear wheel 1312 is larger than the first gear wheel 1310 by a factor greater than 4. For example, in circumstances where the guide catheter 1000 is relatively thicker or heavier, or where an associated interventional device is relatively bulkier, it may be relatively more difficult for an operator to rotate the knob 1300a without adjusting the gear assembly accordingly. In addition, during some interventional procedures, such as delivery and deployment of a replacement valve, an operator may prefer less catheter movement for a given degree of rotation of the knob 1300a (e.g., in order to enable more precision in catheter movement). In some embodiments, the second gear wheel 1312 is larger than the first gear wheel 1310 by a factor of about 4.5 to 10, or about 5 to 8.

Although the foregoing description has been specific to knob 1300a, one of skill in the art will understand that similar features may be utilized with respect to other knobs (e.g., illustrated knob 1300b) included with a given handle embodiment. Some embodiments may include a plurality of steering knobs and/or other actuating components (e.g., one corresponding to each included steerable catheter). Other embodiments include a single actuating component. Further, other embodiments may substitute one or more knobs for another actuating component, such as a lever, slider, etc.

The illustrated embodiment includes a meshed, two-gear assembly for achieving a desired gear ratio between the knob 1300a and control wire tensioning. Other embodiments may include other gear arrangements and/or other force-transmitting components. For example, some embodiments may include a gear assembly utilizing one or more worm gears and/or bevel gears. Some embodiments may include a steering mechanism including one or more of a belt and pulley system, rack and pinion assembly, roller chain assembly, and/or other force-transmitting mechanism.

Figure 18:
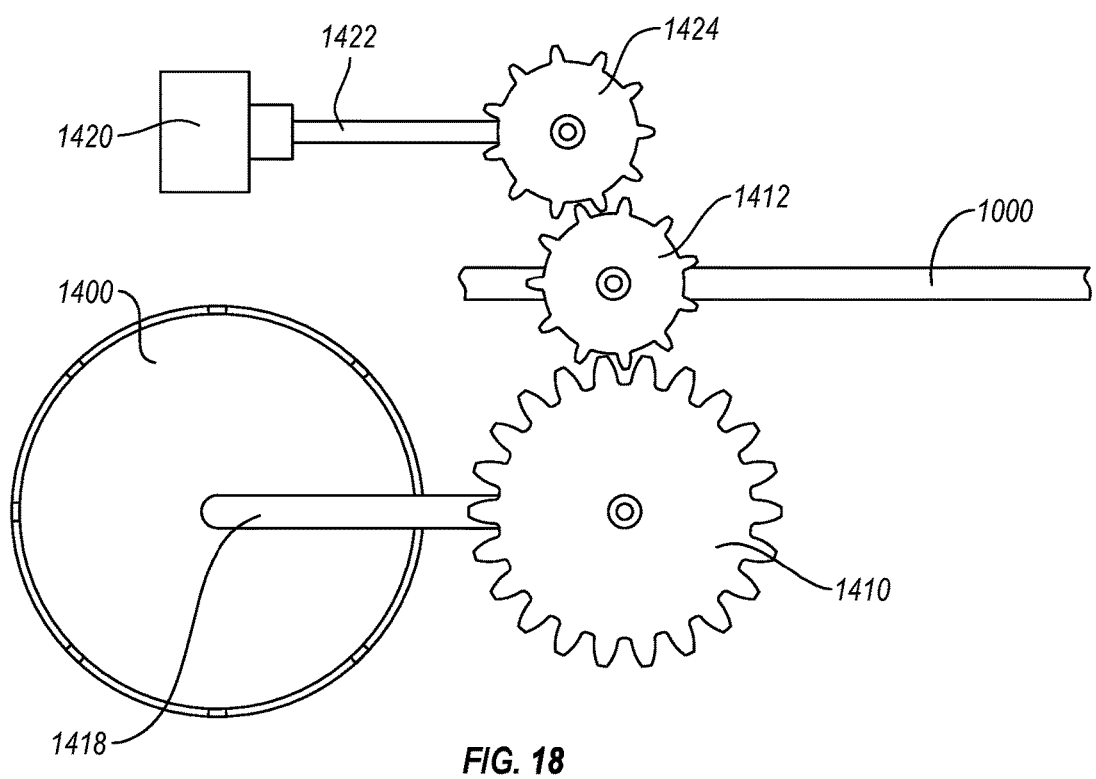
FIGS. 18-20 illustrate various embodiments of steering mechanisms configured for motor-assisted steering of a guide catheter.
Figure 19:
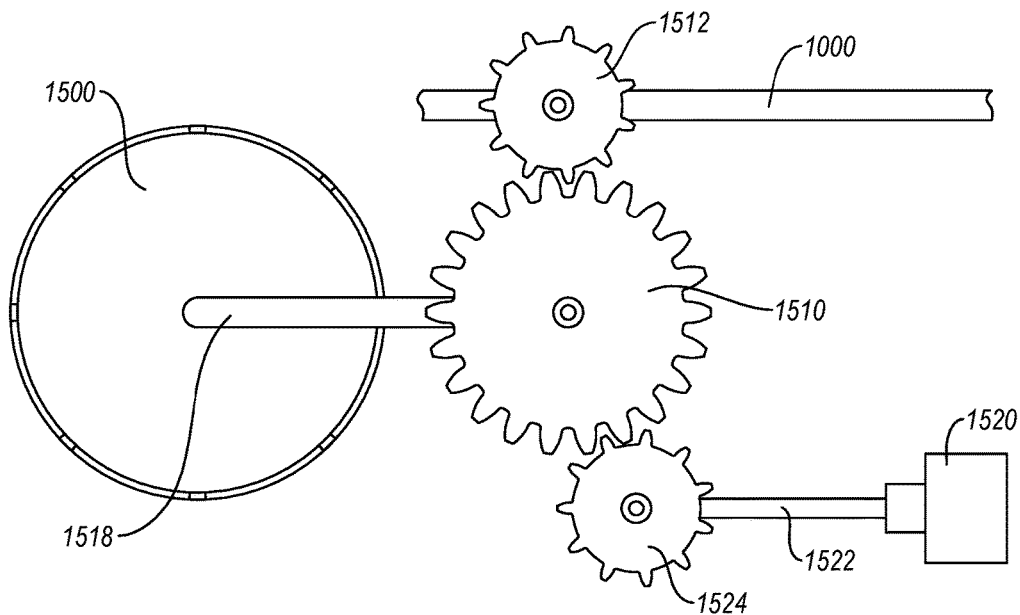
Figure 20:
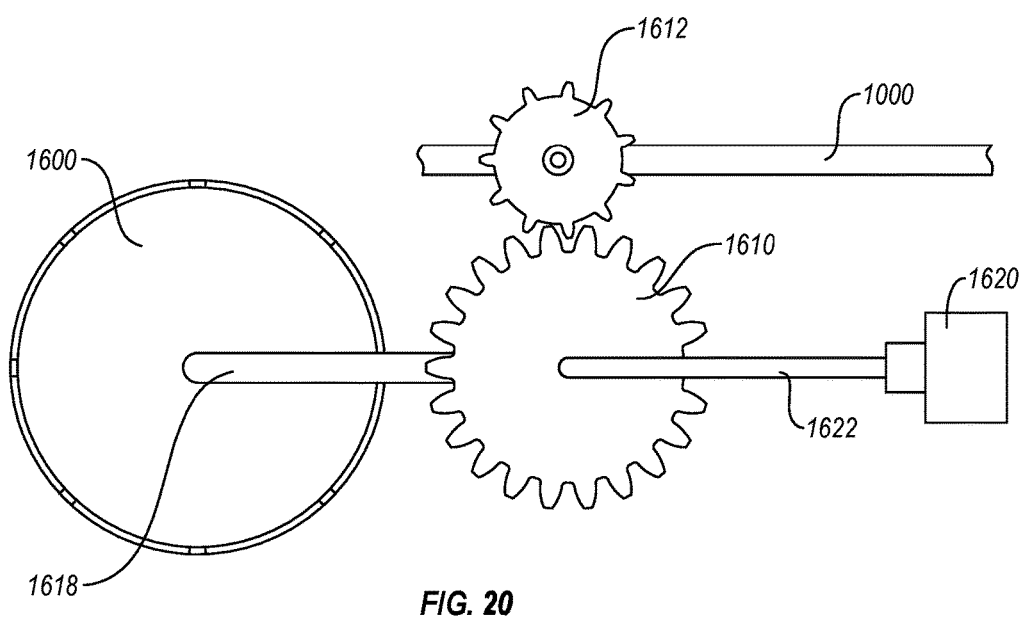

FIGS. 18-20 illustrate embodiments of steering mechanisms configured to provide motor-assisted actuation of one or more associated control wires. In some embodiments, such a motor-assisted configuration may be adapted for use in one or more of the handles and/or steering mechanisms described in relation to FIGS. 15-17. FIG. 18 illustrates a knob 1400 coupled to a post 1418, which is coupled to a first gear wheel 1410. Rotation of the first gear wheel 1410 causes rotation of associated second gear wheel 1412, which causes tensioning of one or more control wires disposed within the corresponding catheter 1000. As shown, the second gear wheel 1412 is also operatively associated with a motor gear wheel 1424, which is coupled to a motor 1420 via a drive shaft 1422. In this exemplary arrangement, the motor 1420 may assist in rotating the second gear wheel 1412 to manipulate one or more control wires within the catheter 1000.

In some embodiments, the motor 1420 includes a motion sensor, torque sensor, and/or revolution speed sensor configured to trigger actuation of the motor 1420 upon sensing a threshold amount of motion, rotation speed, and/or torque. For example, as an operator turns the knob 1400, the one or more sensors can be calibrated such that the motor 1420 is actuated to assist rotation of the second gear wheel 1412. In some embodiments, motor-assisted actuation depends on rotation direction. For example, the motor 1420 may be configured to provide assistance when the knob 1400 is turned to tension one or more control wires, but does not provide assistance (or provides it to a lesser degree) when the knob 1400 is turned to release tension in one or more control wires. The motor 1420 may be a DC motor or an AC motor. In preferred embodiments, the motor 1420 is a DC motor, such as a brushed or brushless DC motor. The motor 1420 may be powered by one or more batteries.

FIGS. 19 and 20 illustrate alternative steering mechanism arrangements also incorporating motor-assisted functionality. The motors and/or other components of the embodiments of FIGS. 19 and 20 may be configured similar to the motor and other corresponding components of the embodiment of FIG. 18. As shown in FIG. 19, a motor 1520 drives a motor gear wheel 1524 via a shaft 1522. The motor gear wheel 1524 is operatively associated with a first gear wheel 1510. The first gear wheel 1510 is coupled to a knob 1500 via post 1518. Rotation of the first gear wheel 1510 causes rotation of a second gear wheel 1512, which functions to adjust the tensioning of one or more control wires of the associated catheter 1000. As shown, the motor 1520 is able to assist in manipulating the one or more control wires of the catheter 1000 by powering the motor gear wheel 1524, which is operatively associated with the first gear wheel 1510. As in other embodiments described herein, the motor 1520 may include or be in communication with one or more sensors for controlling actuation of the motor 1520.

FIG. 20 illustrates another embodiment of a steering mechanism having motor-assisted functionality. In this embodiment, a motor 1620 is arranged to provide direct-drive power to a first gear wheel 1610. In this embodiment, the shaft 1622 is co-extensive with the post 618 extending to a knob 1600. Rotation of the knob 1600 causes rotation of the first gear wheel 1610, which causes rotation of the second gear wheel 1612, which functions to adjust the tensioning of one or more control wires associated with the catheter 1000. As with other embodiments described herein, the motor 1620 may include or be in communication with one or more sensors for controlling actuation of the motor 1620.

Other embodiments of steering systems may include alternatively arranged gearing systems and/or may substitute one or more gearing components for one or more other force-transmitting components. For example, some embodiments may include one or more rack and pinion assemblies, belt and pulley assemblies, roller chain and sprocket assemblies, or other force-transmitting assemblies, in addition to or alternative to the gearing assemblies depicted in the illustrated embodiments.

Figure 21:
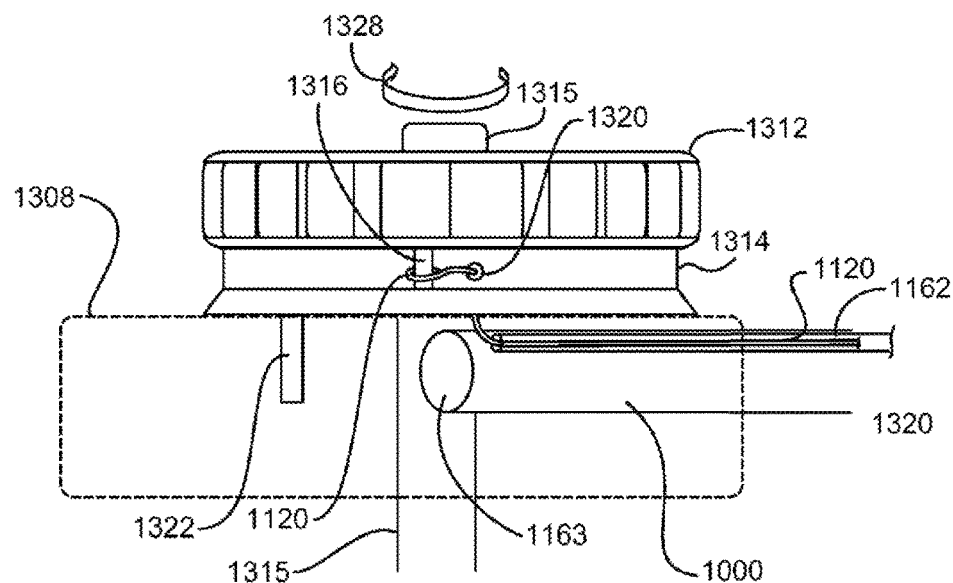
FIGS. 21 and 22 illustrate the exemplary handle assembly of FIGS. 15-17, showing control wire tensioning in response to manipulation of the corresponding controls.
Figure 22:
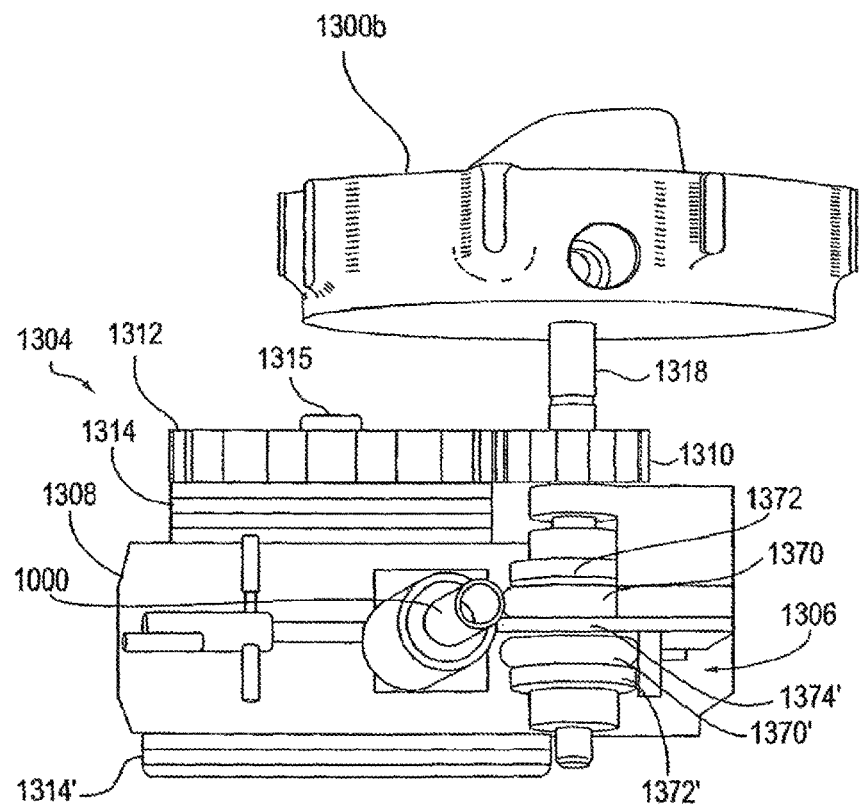

FIGS. 21 and 22 illustrate manipulation of a control wire through rotation of a steering knob. FIGS. 21 and 22 are described in relation to the embodiment depicted in FIGS. 15-17. However, the description may be applied to any of the other steering mechanism embodiments described herein. FIG. 21 shows catheter 1000 passing through base 1308. A control wire 1120 passing through a lumen 1162 in the catheter 1000 emerges from the wall of the catheter 1000, passes through an aperture 1320 in a disk 1314, and is attached to an anchor 1316 on the disk 1314. Rotation of the disk 1314 (indicated by arrow 1328) around a post 1315, by action of the second gear wheel 1312, applies tension to the control wire 1120 by drawing the control wire 1120 through the aperture 1320 and wrapping the control wire 1120 around the disk 1314 as it rotates. Additional rotation of the disk 1314 applies increasing tension to the control wire 1120. To limit the amount of tension applied to the control wire 1120, to limit curvature of the catheter and/or to avoid possible breakage of the control wire 1120, the rotation of the disk 1314 may be restricted by stop peg 1322.

FIG. 22 illustrates an embodiment of a friction assembly 1306. The friction assembly 1306 functions to hold a steering knob, in this example steering knob 1300b, and the associated post 1318 in a rotated position. Here, rotation of the knob 1300b and post 1318 rotates attached first gear wheel 1310. The first gear wheel 1310 actuates the hard stop gear assembly 1304, thereby applying tension to one or more control wires extending through the attached catheter 1000. The steering knob 1300b and post 1318 are held in a rotated position by friction provided by a frictional pad 1370. The frictional pad 1370 is positioned between ring 1372 attached to the post 1318 and a plate 1374' attached to the base 1308. The post 1318 extends from the knob 1300b through the ring 1372, the frictional pad 1370, and then the plate 1374'.

In the illustrated embodiment, the plate 1374' has internal threads which mate with threads on the post 1318. As the knob post 1318 rotates, the threads on the post 1318 advance through the threads on the plate 1374. This draws the ring 1372 closer to the plate 1374', compressing the frictional pad 1370 therebetween. Frictional pad 1370 may be comprised of a material having desirable frictional and compressibility characteristics, such as silicone rubber, natural rubber or synthetic rubbers, to name a few. In preferred embodiments, an ethylene propylene diene terpolymer (EPDM) rubber O-ring is used. Reverse rotation of the post 1318 is resisted by friction of the frictional pad 1370 against the ring 1372. The higher the compression of the frictional pad 1370 the stronger the frictional hold. Therefore, as the steering knob 1300b is rotated and increasing amounts of tension are applied to the control wires 1120, increasing amounts of friction are applied to the ring 1372 to hold the knob 1300b in place.

The embodiment depicted in FIG. 22 also includes additional friction assembly components. One or more control wires passing through catheter 1000 may be attached to the disk 1314'. The disks 1314 and 1314' are arranged so that rotation of steering knob 1300b in one direction applies tension to a first set of one or more control wires via disk 1314 and rotation of steering knob 1300b in the opposite direction applies tension to the a second set of one or more control wires via disk 1314'. The additional friction assembly components include a ring 1372' attached to the post 1318 and a frictional pad 1370' disposed between the ring 1372' and the opposite side of the plate 1374'. As rotation of the steering knob 1300b applies tension to the corresponding one or more control wires via disk 1314', the frictional pad 1370' applies tension to the ring 1372' to hold the post 1318' in place.

Figure 23:
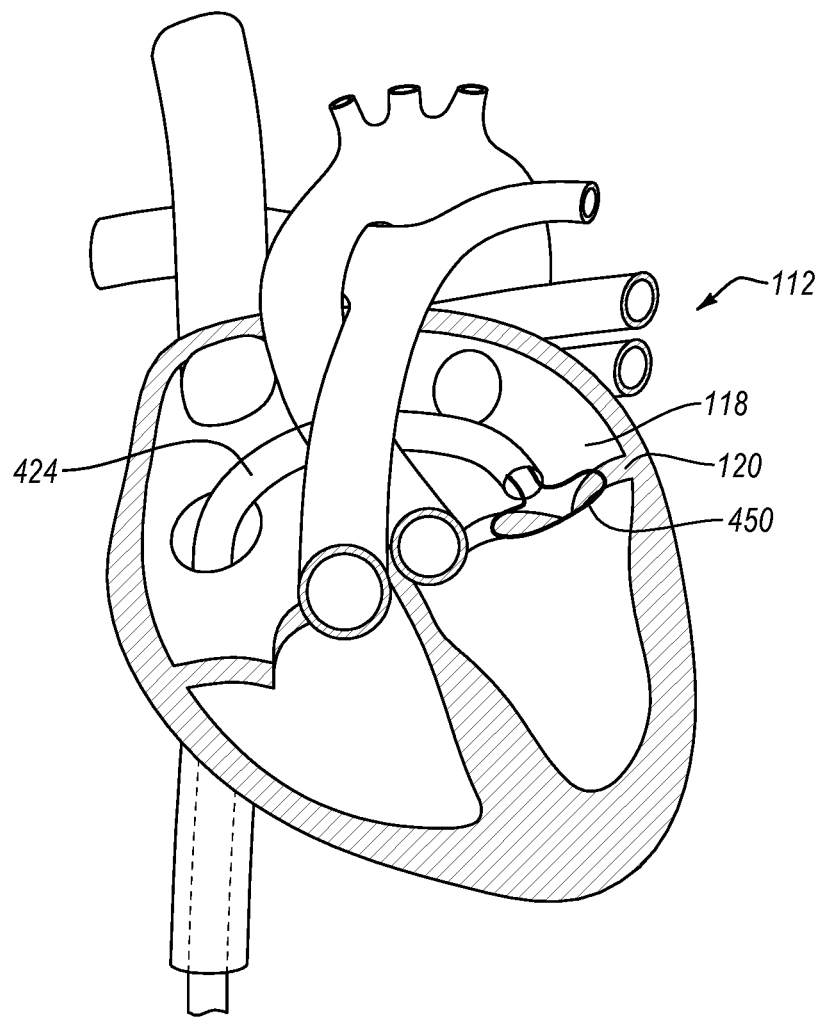
FIGS. 23 and 24 illustrate an exemplary procedure for deploying a replacement mitral valve.
Figure 24:
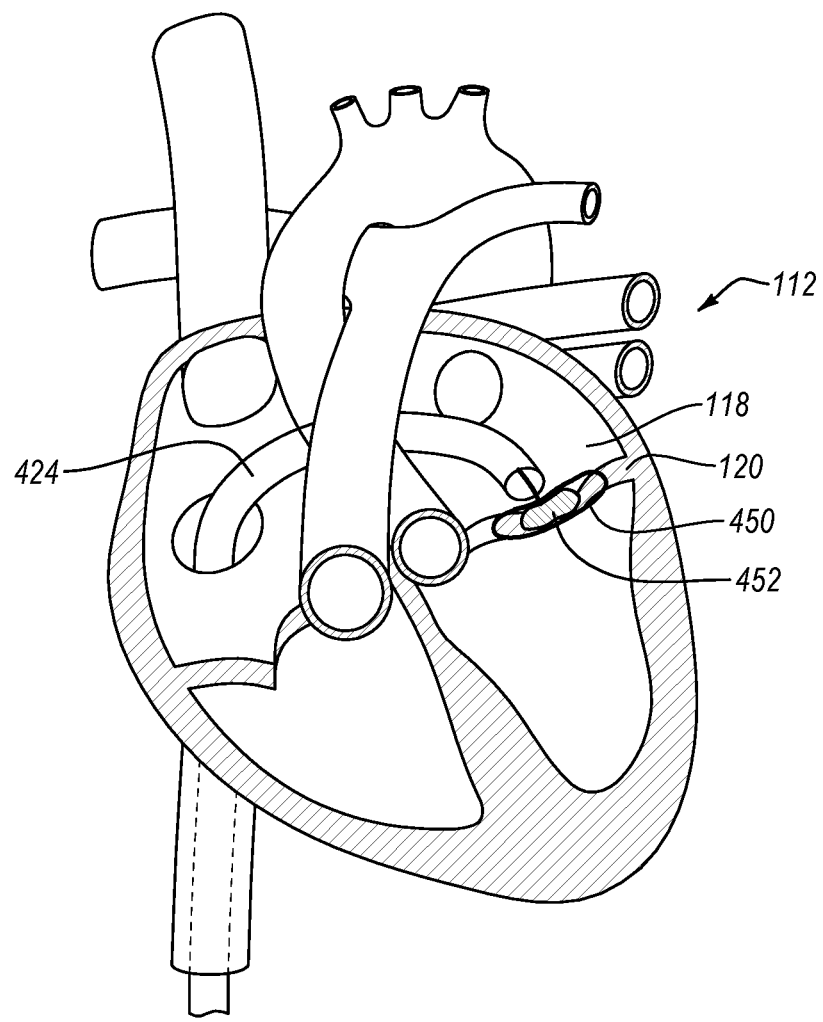

FIGS. 23 and 24 illustrate an exemplary method for delivering a replacement valve utilizing an embodiment of an interventional delivery system described herein. FIG. 23 depicts passage of a delivery catheter 424 into a patient's heart 112. The insertion procedure may be similar to the procedure described in relation to FIG. 2. As shown, the delivery catheter 424 reaches the left atrium 118, where it is oriented with respect to the mitral valve annulus 120. For example, the delivery catheter 424 can be configured to enable medial-lateral (M/L) and/or anterior-posterior (A/P) positioning so that one or more replacement valve components may be properly positioned for deployment within the patient's heart 112. In some embodiments, each of M/L movement and A/P movement may be controlled via separate knobs, which may be configured similar to knobs 1300a and 1300b, or other knobs described herein.

Positioning of the guide catheter 424 as shown allows sequential delivery of a multi-component replacement valve. For example, FIG. 23 illustrates deployment of an outer frame 450 at the mitral valve annulus 120. In some embodiments, the guide catheter 424 may remain in place while the delivery system used to deploy the outer frame 450 is removed from the guide catheter 424. Subsequently, a secondary delivery system may be inserted into the guide catheter 424 and routed to the targeted mitral valve annulus 120 through the already substantially positioned guide catheter 424. As shown in FIG. 24, an inner valve 452 may then be deployed and anchored/docked to the outer frame 450 using the secondary delivery system.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to guide catheters, sleeves, and/or valve delivery systems of FIGS. 6-13D may be combinable with any element described in relation to a handle and/or steering mechanism embodiment illustrated in FIGS. 15-22.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A delivery system configured for delivering an interventional device to a targeted treatment area within a body, the delivery system comprising:
 a steerable catheter having a proximal end and a distal end; and
 an interventional device delivery system positioned within the steerable catheter and configured to be translatable within the steerable catheter so as to selectively deploy the interventional device beyond the distal end of the steerable catheter, the interventional device delivery system comprising:

a shaft; and a sheath operatively coupled to the shaft, the sheath having a first portion, a second portion, and a space defined by the first portion and the second portion, the first portion of the sheath enclosing a first portion of the interventional device, the second portion of the sheath enclosing a second portion of the interventional device, and the first and second portions of the sheath being selectively moveable relative to one another and relative to the interventional device so as to:

selectively deploy the first portion of the interventional device from the sheath while maintaining the second portion of the interventional device within the sheath, or alternatively, selectively deploy the second portion of the interventional device from the sheath while maintaining the first portion of the interventional device within the sheath, and once one portion of the interventional device is deployed and positioned at the targeted treatment area, move the other portion of the sheath to selectively deploy the other portion of the interventional device, wherein a portion of the sheath is translatable upon subjection to a hydraulic force, from a fluid ejected into the space enclosing the interventional device prior to the sheath separating to deploy the interventional device, to deploy one of the first portion or the second portion of the interventional device.

2. The delivery system of claim 1, wherein at least a portion of the steerable catheter includes a notch, and wherein at least a portion of the interventional device delivery system includes a corresponding extension lodging within the notch to lock rotation of the interventional device delivery system with respect to the steerable catheter.

3. The delivery system of claim 1, wherein the interventional device delivery system includes a distal tip enclosing a distal section of a replacement heart valve, as the interventional device, and includes a proximal sheath enclosing a proximal section of the replacement heart valve, the distal tip being distally translatable relative to the replacement heart valve, and the proximal sheath being proximally translatable relative to the replacement heart valve.

4. The delivery system of claim 3, wherein the distal tip is distally translatable upon subjection to a distally oriented hydraulic force to deploy the distal section of the replacement heart valve, and wherein the proximal sheath is proximally translatable to deploy the proximal section of the replacement heart valve.

5. The delivery system of claim 1, wherein the sheath defines an inter-luminal space through which at least a portion of the shaft extends, and wherein the shaft includes a plurality of fluid ports enabling the passage of fluid into the inter-luminal space so as to cause at least a portion of the sheath to translate proximally relative to the interventional device to deploy the interventional device.

6. The delivery system of claim 5, wherein the sheath includes a proximal wall that defines the proximal extent of the inter-luminal space, the proximal wall enabling the sheath to be translated proximally as a result of a hydraulic force imparted by the fluid.

7. The delivery system of claim 1, wherein the interventional device delivery system includes a tether detachably coupled to the interventional device, the tether and the interventional device forming a magnetic coupling upon passage of electric current through the tether, the tether being selectively decoupled from the replacement heart valve upon cessation of the electric current.

8. The delivery system of claim 1, wherein the interventional device delivery system includes a tether detachably coupled to the interventional device, the tether including a meltable portion and a heat-transmitting portion such that the transmission of heat through the heat-transmitting portion causes sufficient melting of the meltable portion to decouple the tether from the interventional device.

9. The delivery system of claim 1, wherein the steerable catheter includes one or more control wires, each control wire coupled to a control of the handle and to the distal end of the steerable catheter such that tensioning of the control wire causes corresponding deflection of the steerable catheter, wherein the one or more control wires are formed from a titanium or titanium alloy material and have an ultimate tensile strength within a range of 700 to 1500 MPa.

10. The delivery system of claim 1 further comprising a handle coupled to the proximal end of the steerable catheter, the handle having one or more controls and one or more corresponding steering mechanisms enabling steering of the steerable catheter.

11. The delivery system of claim 10, wherein the handle includes a rotatable control operatively coupled to a control wire tensioning wheel through a gear assembly, the gear assembly being arranged so that rotation of the wire tensioning wheel relative to rotation of the rotatable control is reduced by a factor greater than 8.

12. The delivery system of claim 10, wherein the handle includes a motor configured to provide motor-assisted tensioning of one or more control wires.

13. The delivery system of claim 1, wherein the steerable catheter includes a plurality of cuts arranged to enable one or more of preferential bending or increased flexibility of the steerable catheter.

14. A delivery system configured for delivering a replacement heart valve to a targeted heart valve within a body, the delivery system comprising:

a catheter configured to house a deployable replacement valve, the catheter having a proximal end and a distal end;

a distal tip enclosing a distal section of the replacement valve, the distal tip being distally translatable relative to the replacement valve; and a sheath enclosing a proximal section of the replacement valve, the sheath being proximally translatable relative to the replacement valve, the distal tip and the sheath forming a space for the replacement heart valve, wherein the distal tip is distally translatable upon subjection to a distally oriented hydraulic force, from a fluid ejected into and filling the space of the sheath in a closed state in which the sheath is enclosing the replacement valve, to deploy the distal section of the replacement valve, and wherein the sheath is proximally translatable to deploy the proximal section of the replacement valve.

15. The delivery system of claim 14, wherein the interventional device delivery system includes a tether detachably coupled to the replacement heart valve, the tether and the replacement heart valve forming a magnetic coupling upon passage of electric current through the tether, the tether being selectively decoupled from the replacement heart valve upon turning off the electric current.

16. The delivery system of claim 14, wherein the interventional device delivery system includes a tether detachably coupled to the replacement heart valve, the tether including a meltable portion and a heat-transmitting portion such that the transmission of heat through the heat-transmitting portion causes sufficient melting of the meltable portion to decouple the tether from the replacement heart valve.

17. A delivery system configured for delivering a replacement heart valve to a targeted heart valve within a body, the delivery system comprising:

a catheter configured to house a deployable replacement valve, the catheter having a proximal end and a distal end; and a sheath enclosing the replacement heart valve, the sheath also defining an inter-luminal space through which at least a portion of a shaft extends, the shaft including a plurality of fluid ports enabling the passage of fluid into the inter-luminal space so as to cause the sheath to translate proximally relative to the replacement heart valve to deploy the replacement heart valve, the inter-luminal space receiving the fluid from the plurality of fluid ports also includes the replacement heart valve, the fluid being present within the inter-luminal space prior to the sheath translating proximally relative to the replacement heart valve to deploy the replacement heart valve.

18. The delivery system of claim 17, wherein the sheath includes a proximal wall that defines the proximal extent of the inter-luminal space, the proximal wall enabling the sheath to be translated proximally as a result of a hydraulic force imparted by the fluid.

19. The delivery system of claim 17, wherein the interventional device delivery system includes a tether detachably coupled to the replacement heart valve, the tether and the replacement heart valve forming a magnetic coupling upon passage of electric current through the tether, the tether being selectively decoupled from the replacement heart valve upon turning off the electric current.

20. The delivery system of claim 17, wherein the interventional device delivery system includes a tether detachably coupled to the replacement heart valve, the tether including a meltable portion and a heat-transmitting portion such that the transmission of heat through the heat-transmitting portion causes sufficient melting of the meltable portion to decouple the tether from the replacement heart valve.

* * * * *